US012788587B2

(12) United States Patent
Lee

(10) Patent No.: US 12,788,587 B2
(45) Date of Patent: Nov. 10, 2026

(54) JOINT REPLACEMENT ALIGNMENT GUIDES, SYSTEMS AND METHODS OF USE AND ASSEMBLY

(71) Applicant: Paragon 28, Inc., Englewood, CO (US)

(72) Inventor: Daniel J. Lee, Denver, CO (US)

(73) Assignee: Paragon 28, Inc., Englewood, CO (US)

( * ) Notice: Subject to any disclaimer, the term of this patent is extended or adjusted under 35 U.S.C. 154(b) by 778 days.

(21) Appl. No.: 17/659,411

(22) Filed: Apr. 15, 2022

(65) Prior Publication Data

US 2022/0233332 A1 Jul. 28, 2022

Related U.S. Application Data

(63) Continuation of application No. 17/304,046, filed on Jun. 14, 2021, now Pat. No. 11,304,823, which is a (Continued)

(51) Int. Cl.

| | |
|---|---|
| ***A61B 17/15*** | (2006.01) |
| ***A61B 17/17*** | (2006.01) |

(Continued)

(52) U.S. Cl.

CPC ............ *A61F 2/4606* (2013.01); *A61B 17/15* (2013.01); *A61B 17/7291* (2013.01); *A61F 2/4202* (2013.01); *A61F 2/46* (2013.01); *A61B 17/17* (2013.01); *A61B 17/1775* (2016.11); *A61B 2017/681* (2013.01); *A61F 2002/4628* (2013.01); *A61F 2002/4687* (2013.01)

(58) Field of Classification Search

CPC ........ A61F 2/4606; A61F 2/4202; A61F 2/46; A61F 2002/4628; A61B 17/15; A61B 17/1775; A61B 2017/681

See application file for complete search history.

(56) References Cited

U.S. PATENT DOCUMENTS 4,893,619 A * 1/1990 Dale ..................... A61B 17/15 606/82
5,540,696 A 7/1996 Booth, Jr.
(Continued)

FOREIGN PATENT DOCUMENTS

WO 2005048851 6/2005
WO 2010011978 1/2010

OTHER PUBLICATIONS

International Search Report and Written Opinion of the International Searching Authority for PCT/US2019/066408, Feb. 11, 2020, 11 pages.
(Continued)

*Primary Examiner* — Tracy L Kamikawa
(74) *Attorney, Agent, or Firm* — Heslin Rothenberg Farley & Mesiti P.C.; Jacquelyn A. Graff, Esq.

(57) ABSTRACT

Instruments, devices, systems and methods for maintaining, correcting and/or fusing joint deformities are disclosed. The system includes a first translation mechanism, a second translation mechanism coupled to the first translation mechanism, and a third translation mechanism coupled to the second translation mechanism. Methods of assembling and using the alignment guides for maintaining, correcting and/or fusing joint deformities are also disclosed.

10 Claims, 32 Drawing Sheets

Related U.S. Application Data continuation of application No. PCT/US2019/066408, filed on Dec. 13, 2019.

(60) Provisional application No. 62/899,655, filed on Sep. 12, 2019, provisional application No. 62/899,703, filed on Sep. 12, 2019, provisional application No. 62/899,740, filed on Sep. 12, 2019, provisional application No. 62/779,436, filed on Dec. 13, 2018.

(51) Int. Cl.

| | |
|---|---|
| ***A61B 17/72*** | (2006.01) |
| ***A61F 2/42*** | (2006.01) |
| ***A61F 2/46*** | (2006.01) |
| *A61B 17/68* | (2006.01) |

(56) References Cited

U.S. PATENT DOCUMENTS

| | | | | |
|---|---|---|---|---|
| 6,030,391 | A | 2/2000 | Brainard | |
| 7,029,477 | B2 | 4/2006 | Grimm | |
| 7,641,661 | B2 * | 1/2010 | Steffensmeier | A61B 17/157 606/88 |
| 8,808,303 | B2 | 8/2014 | Stemniski | |
| 9,220,518 | B2 | 12/2015 | Neal et al. | |
| 9,445,823 | B2 * | 9/2016 | Harris | A61B 17/15 |
| 11,304,823 | B2 * | 4/2022 | Lee | A61F 2/46 |
| 11,446,072 | B2 * | 9/2022 | Abedian | A61B 17/72 |
| 2005/0021039 | A1 | 1/2005 | Cusick | |
| 2008/0114369 | A1 | 5/2008 | Bastian | |
| 2009/0234360 | A1 * | 9/2009 | Alexander | A61B 17/15 606/88 |
| 2010/0121334 | A1 | 5/2010 | Couture | |
| 2011/0208093 | A1 | 8/2011 | Gross | |
| 2011/0218543 | A1 | 9/2011 | van der Walt | |
| 2015/0157339 | A1 | 6/2015 | McGinley | |
| 2016/0367270 | A1 * | 12/2016 | Garlock | A61B 17/1739 |
| 2018/0146970 | A1 | 5/2018 | Luna et al. | |
| 2018/0263639 | A1 * | 9/2018 | McGinley | A61F 2/4606 |
| 2018/0280038 | A1 | 10/2018 | Goble | |
| 2020/0060690 | A1 | 2/2020 | Woodward | |
| 2021/0212704 | A1 | 7/2021 | Wong | |

OTHER PUBLICATIONS

Extended European Search Report issued in European Patent Application No. 19895132.9, Sep. 16, 2022, 9 pages.

Karl M. Schweitzer Jr., et al., Total Ankle Arthroplasty with a Modern Fixed-Bearing System: The Salto Talaris Prothesis, Journal Bone Joint Surgery Am., Jun. 5, 2013, 1002-1011, vol. 95(11).

* cited by examiner

500

500

600

600

JOINT REPLACEMENT ALIGNMENT GUIDES, SYSTEMS AND METHODS OF USE AND ASSEMBLY

CROSS REFERENCE TO RELATED APPLICATION

This application is a continuation of U.S. Continuation application Ser. No. 17/304,046 filed Jun. 14, 2021 and entitled Joint Replacement Alignment Guides, Systems and Methods of Use and Assembly, which is a continuation of PCT/US2019/066408 filed on Dec. 13, 2019 and entitled Joint Replacement Alignment Guides, Systems and Methods of Use and Assembly, which claims priority benefit under 35 U.S.C. § 119(e) of U.S. Provisional Application No. 62/899,703 filed Sep. 12, 2019 and entitled Joint Replacement Alignment Guides, Systems and Methods of Use and Assembly, U.S. Provisional Application No. 62/899,655 filed Sep. 12, 2019 and entitled Alignment Instruments and Methods for Use in Total Ankle Replacement, U.S. Provisional Application No. 62/899,740 filed Sep. 12, 2019 and entitled Joint Replacement Alignment Guides, Systems and Methods of Use and Assembly, and U.S. Provisional Application No. 62/779,436 filed Dec. 13, 2018 and entitled Joint Replacement Systems and Methods of Use and Assembly, which are incorporated herein by reference in their entireties.

TECHNICAL FIELD

The present disclosure relates generally to general, podiatric, and orthopaedic surgery related to joint deformities. More specifically, but not exclusively, the present disclosure relates to guides, devices, instruments, systems and methods for maintaining, correcting and/or resurfacing joint surfaces.

BACKGROUND OF THE INVENTION

Total ankle replacement (TAR), or ankle arthroplasty, is a surgical procedure to replace deformed and/or damaged articular surfaces of the human ankle joint with a prosthetic joint while preserving the functional range of motion (ROM) of the ankle joint.

Achieving a stable replacement ankle joint that provides for full articulation/motion (e.g., achieving a range of motion of a typical "healthy" ankle joint) can be difficult with currently available TAR surgical procedures and instruments. The currently available systems may not provide for proper sizing and positioning, orientating, aligning of the tibial component with respect to the distal end of a tibia, of the talus component with respect to the proximal end of a talus, or of the insert or spacer therebetween.

Thus, it is an object of the present disclosure to overcome one or more of the above-described drawbacks and/or disadvantages of the currently available systems.

SUMMARY OF THE INVENTION

The present disclosure is directed toward implants, devices and methods for use in maintaining, correcting and/or resurfacing joint surfaces.

In one aspect of the present disclosure provided herein, is an alignment guide system. The system including a first translation mechanism, a second translation mechanism coupled to the first translation mechanism, and a third translation mechanism coupled to the second translation mechanism.

In another aspect of the present disclosure provided herein, is method for assembling an alignment guide system. The method includes obtaining a first translation mechanism, a second translation mechanism, and a third translation mechanism. The method also includes coupling the first translation mechanism to the second translation mechanism and coupling the third translation mechanism to a housing of the second translation mechanism.

In yet another aspect of the present disclosure provided herein, is method for using an alignment guide system. The method includes obtaining an alignment guide system and coupling the alignment guide system to a patient's tibia. The method further includes translating the alignment guide system in at least one of a medial-lateral direction, a distal-proximal direction, and a varus-valgus direction.

In yet another aspect of the present disclosure provided herein, is a kit. The kit including a plurality of alignment guide systems as well as alignment attachments, resection attachments and the like for the performing a TAR procedure.

These and other objects, features and advantages of this disclosure will become apparent from the following detailed description of the various aspects of the disclosure taken in conjunction with the accompanying drawings.

BRIEF DESCRIPTION OF THE DRAWINGS

The accompanying drawings, which are incorporated in and constitute a part of the specification, illustrate embodiments of the disclosure and together with the detailed description herein, serve to explain the principles of the disclosure. It is emphasized that, in accordance with the standard practice in the industry, various features are not drawn to scale. In fact, the dimensions of the various features may be arbitrarily increased or reduced for clarity of discussion. The drawings are only for purposes of illustrating preferred embodiments and are not to be construed as limiting the disclosure.

DETAILED DESCRIPTION FOR CARRYING OUT THE INVENTION

Figure 2:
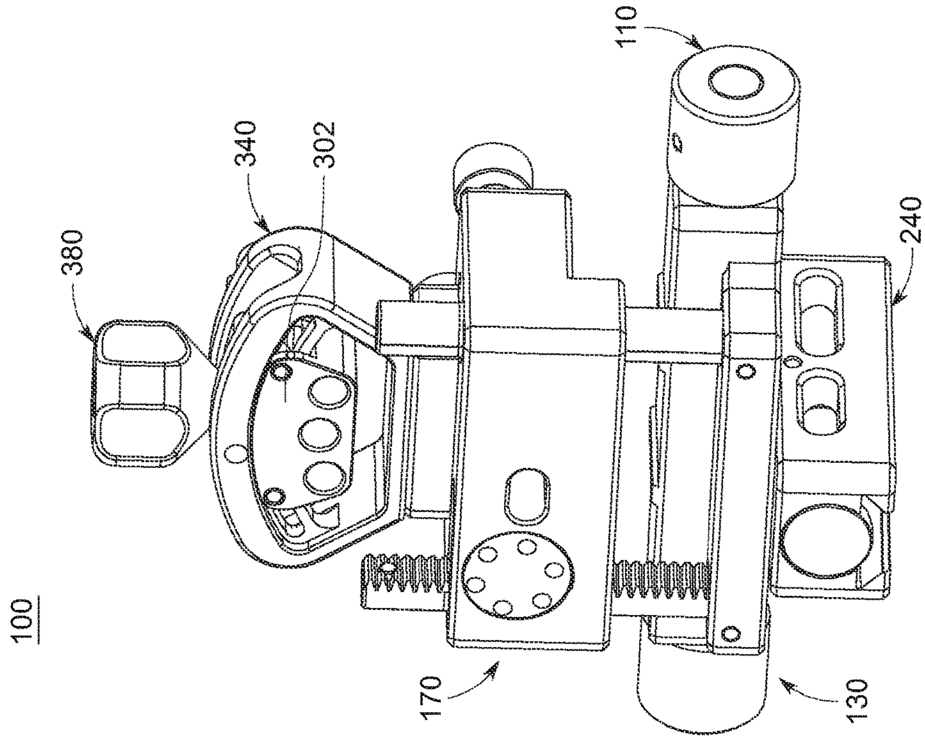
FIG. 2 is a second perspective view of the alignment guide of FIG. 1, in accordance with an aspect of the present disclosure.

Generally stated, disclosed herein are guides, devices, instruments, systems, and methods for maintaining, correcting and/or resurfacing joint surfaces. Further, methods for using the guides, devices, instruments, systems, and methods for maintaining, correcting and/or resurfacing joint surfaces are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the ankle, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right leg may be mirrored so that they likewise function with the left leg. Further, the devices, systems, instrumentation and methods, and the aspects, components, features and the like thereof, disclosed herein are described with respect to the leg for brevity purposes, but it should be understood that the devices, systems, instrumentation and methods may be used with other bones of the body having similar structures.

Referring to the drawings, wherein like reference numerals are used to indicate like or analogous components throughout the several views, and with particular reference to FIGS. 1-31, the instruments, devices, implants, systems, and methods of using the instruments, devices, implants, and systems for a total ankle replacement (TAR) procedure are shown. The total ankle replacement procedure may include, for example, an alignment procedure, an initial resection procedure, a trialing and chamfer resection procedure, a final trialing and peg preparation procedure, and an implantation procedure.

Figure 1:
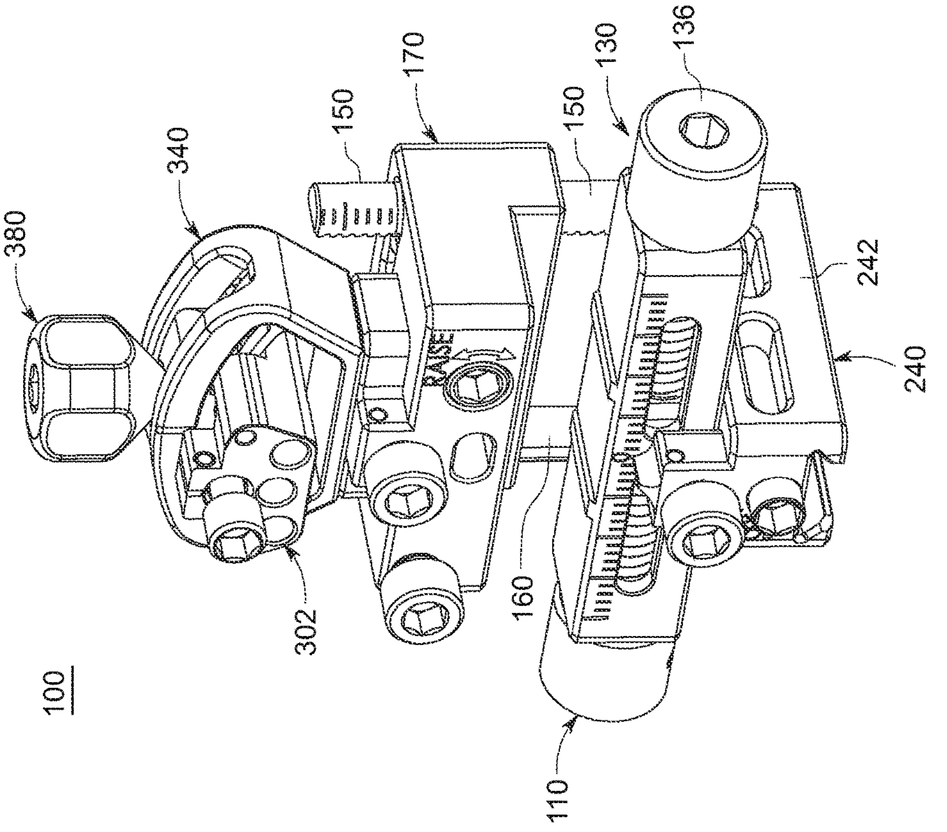
FIG. 1 is a first perspective view of an alignment guide, in accordance with an aspect of the present disclosure.
Figure 4:
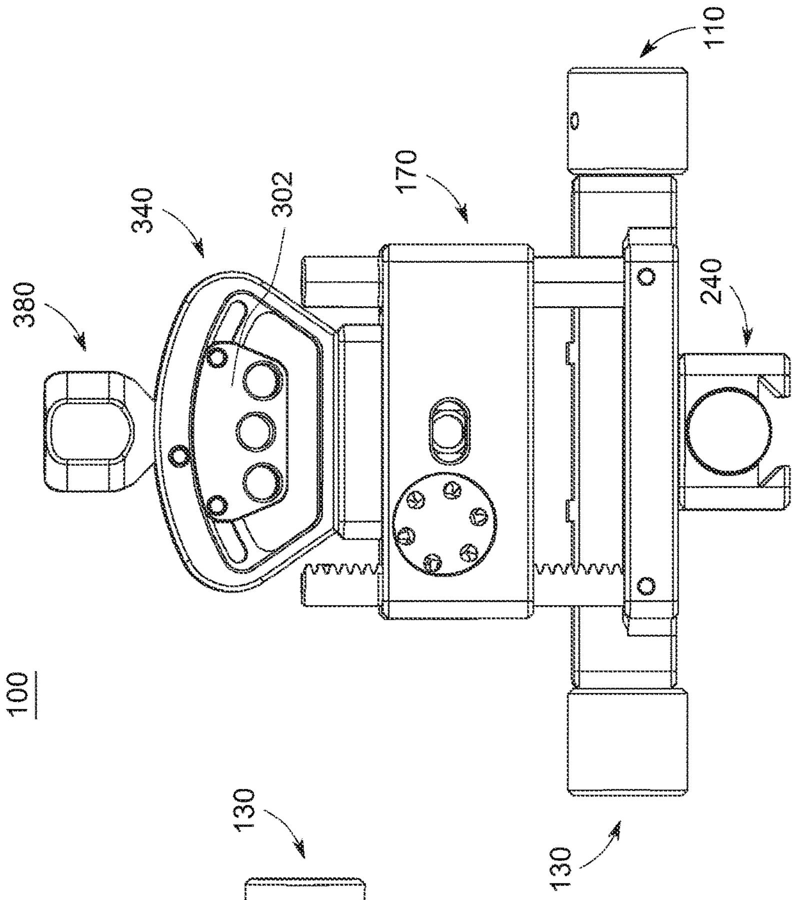
FIG. 4 is a second side view of the alignment guide of FIG. 1, in accordance with an aspect of the present disclosure.
Figure 3:
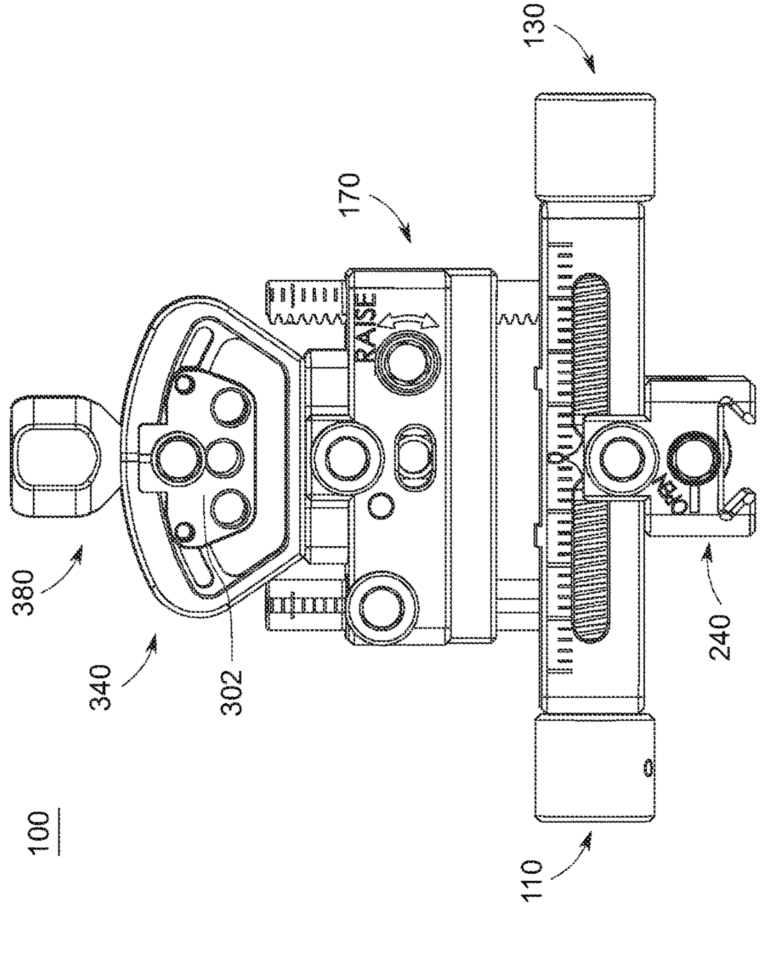
FIG. 3 is a first side view of the alignment guide of FIG. 1, in accordance with an aspect of the present disclosure.
Figure 6:
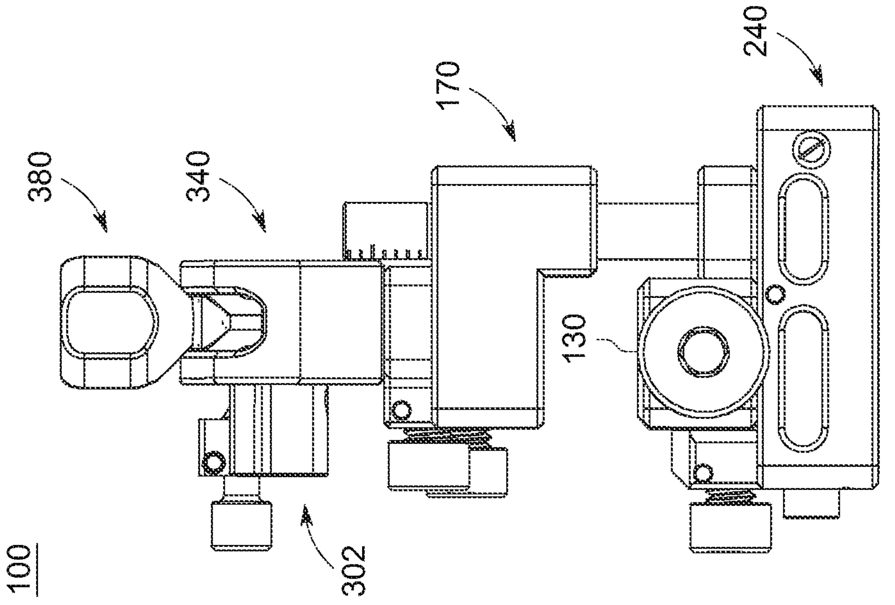
FIG. 6 is a second end view of the alignment guide of FIG. 1, in accordance with an aspect of the present disclosure.
Figure 5:
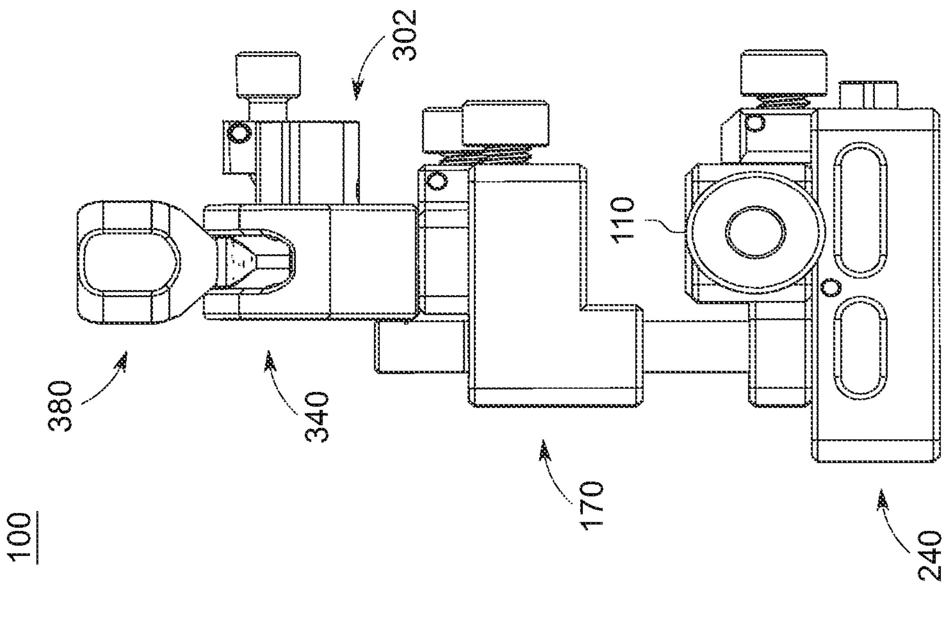
FIG. 5 is a first end view of the alignment guide of FIG. 1, in accordance with an aspect of the present disclosure.
Figure 7:
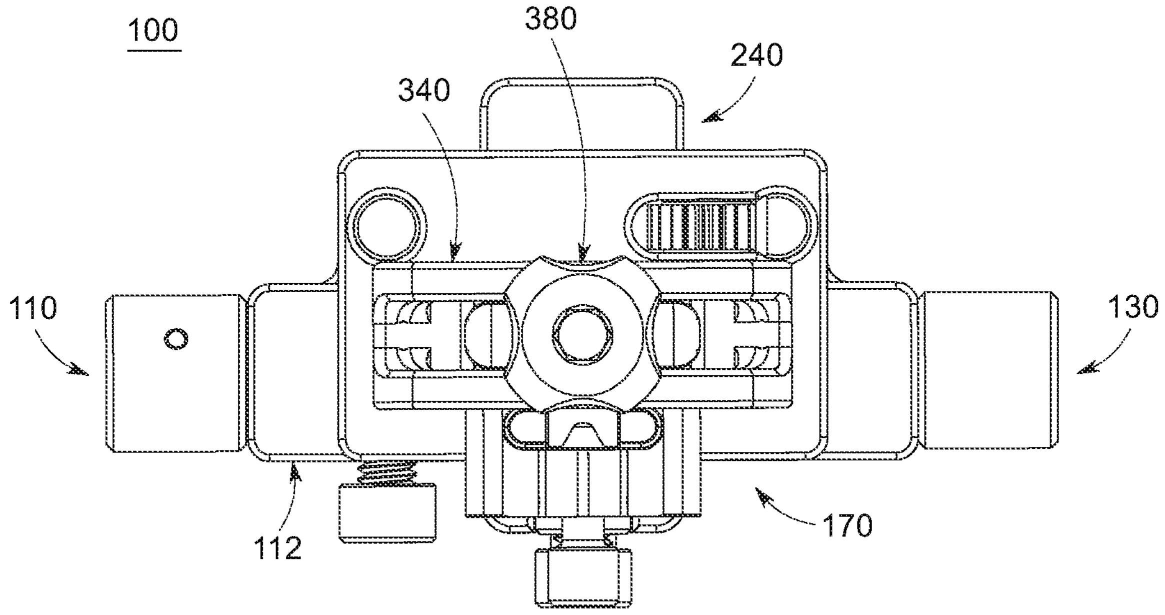
FIG. 7 is a top view of the alignment guide of FIG. 1, in accordance with an aspect of the present disclosure.
Figure 8:
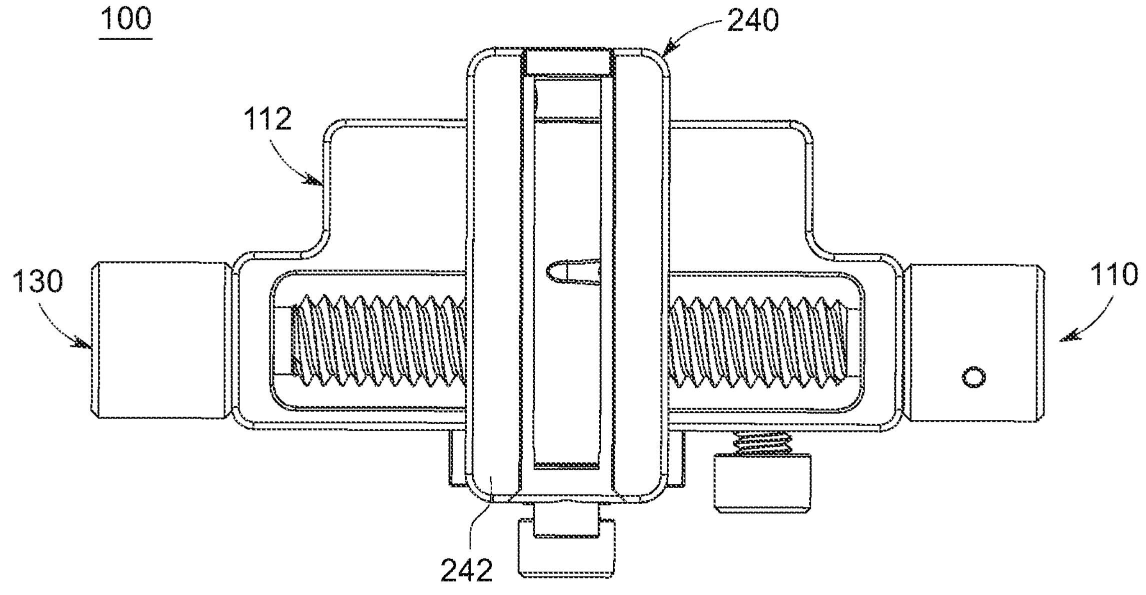
FIG. 8 is a bottom view of the alignment guide of FIG. 1, in accordance with an aspect of the present disclosure.

Referring now to FIGS. 1-62, alignment guides for TAR surgery are shown. A first alignment guide 100 is shown in FIGS. 1-25. As shown in FIG. 1, the alignment guide or fast-track alignment guide 100 includes a first translation mechanism or medial lateral adjustment member 110, a second translation mechanism or distal proximal adjustment member 170, and a third translation mechanism or varus-valgus adjustment member 300. The second translation mechanism 170 is movably coupled to the first translation mechanism 110 by distal proximal translating members 150, 160. The third translation mechanism 300 is detachably coupled to the second translation mechanism 170.

Figure 19:
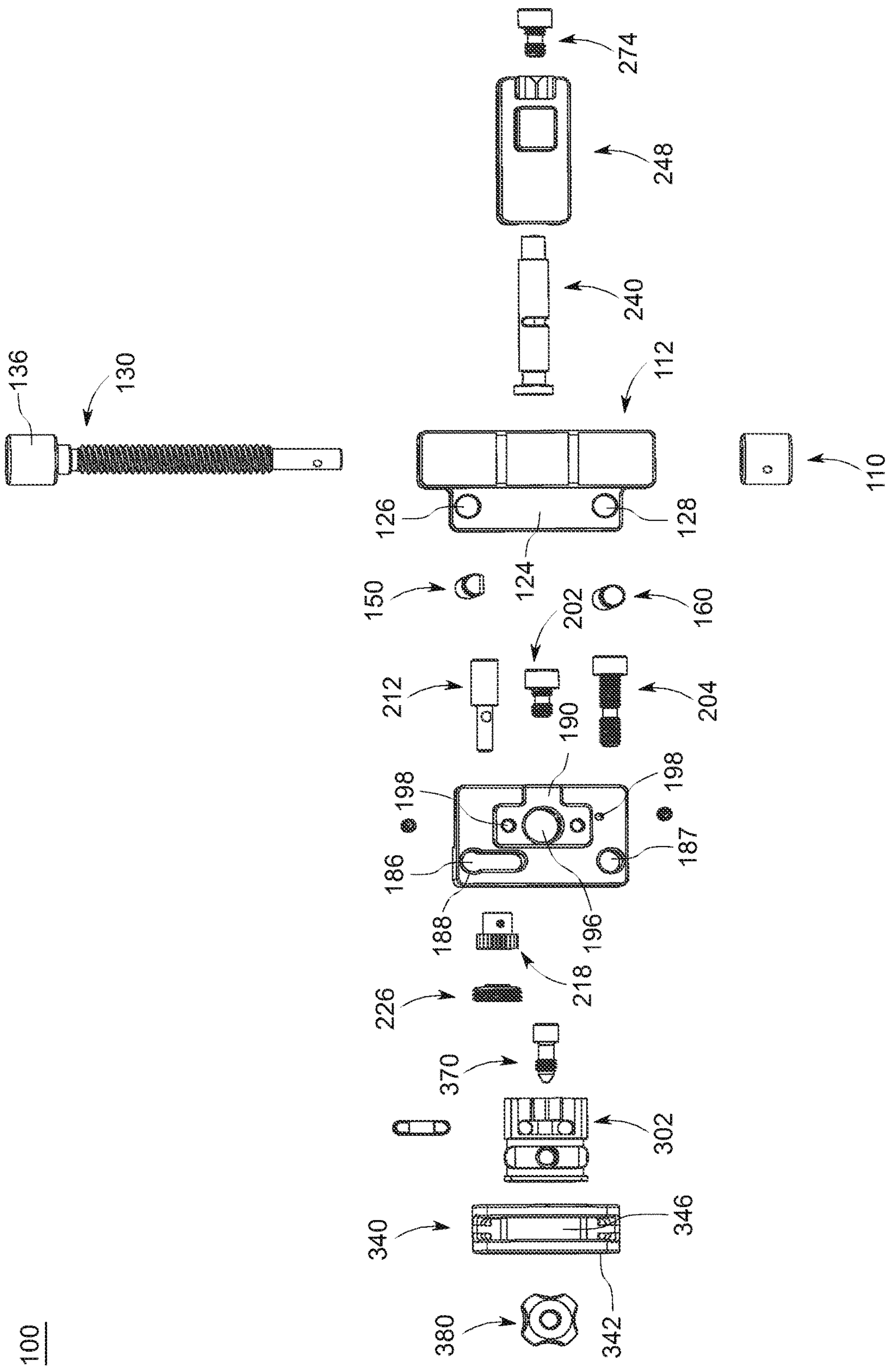
FIG. 19 is an exploded, top view of the alignment guide of FIG. 1, in accordance with an aspect of the present disclosure.
Figure 20:
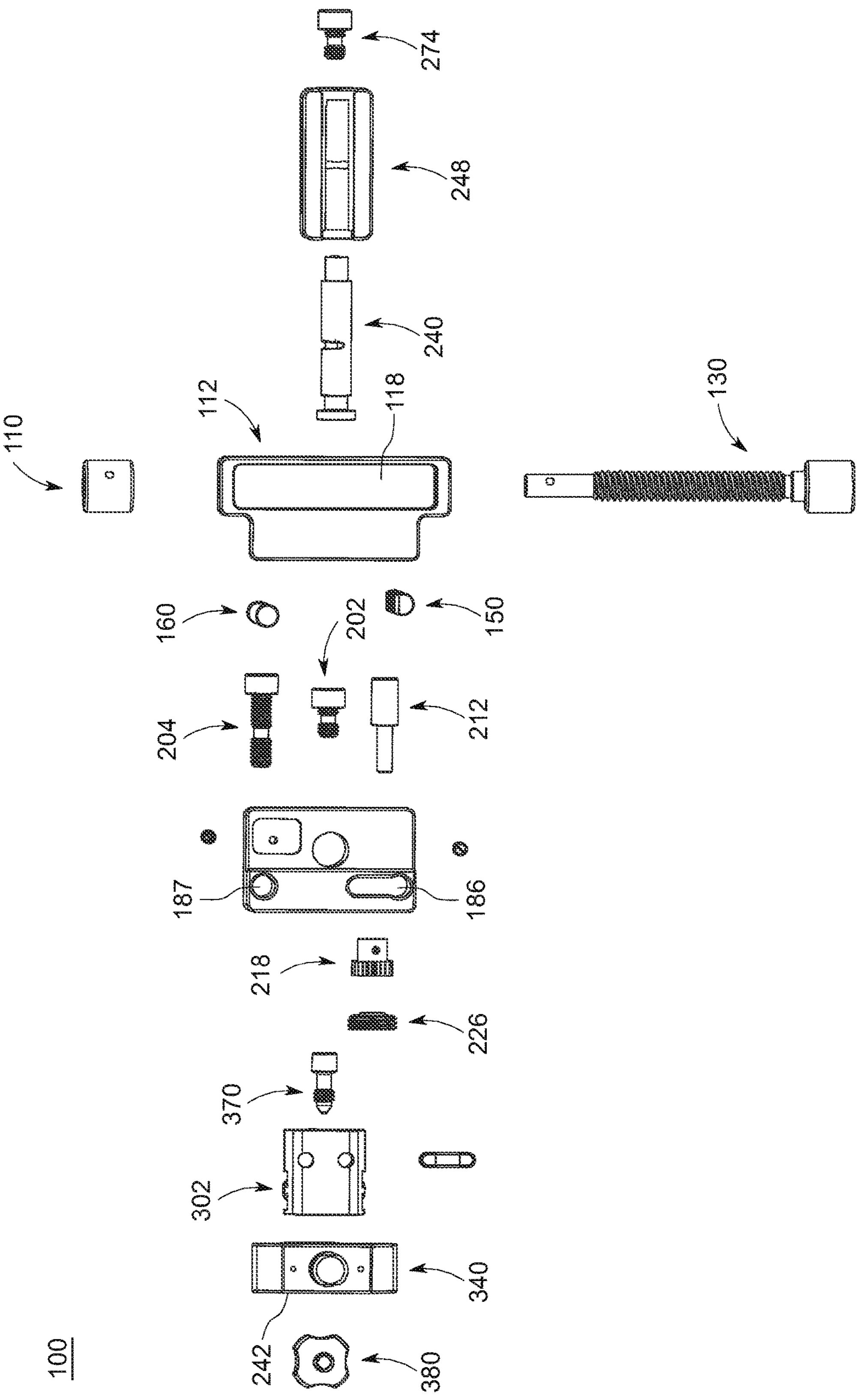
FIG. 20 is an exploded, bottom view of the alignment guide of FIG. 1, in accordance with an aspect of the present disclosure.

Referring now to FIGS. 11-20, the first translation mechanism 110 includes a housing 112, a fastening member or screw 130 received within the housing 112, and a coupling member or cap 140 secured to the fastening member 130. The housing 112 may include a first opening 114 positioned at a first end and extending into the housing 112 and a second opening 116 positioned at a second end and extending into the housing 112. The first opening 114 may be aligned with the second opening 116 to receive the fastening member 130. The housing 112 may further include a cavity 118 extending into the housing 112 from a bottom or distal surface. The cavity 118 may intersect with the first opening 114 and/or the second opening 116. The cavity 118 may also receive a portion of the fastening member 130 when the first translation mechanism 110 is assembled. In addition, the housing 112 may include at least one window 120 extending from a first side of the housing 112 into the cavity 118. The at least one window 120 may also or alternatively extend along at least a portion of a first side of the housing 112. The housing 112 may also include a plurality of dimension markings 122 positioned along at least a portion of the first side of the housing 112. Further, the housing 112 includes a foot or extension member 124 extending away from a second side of the housing 112. The extension member 124 may be, for example, positioned near the distal end of the second side of the housing 112. As shown in FIG. 19, the extension member 124 may include a first recess 126 positioned at the first end of the housing 112 and a second recess 128 positioned at the second end of the housing 112.

With continued reference to FIGS. 11-20, the fastening member 130 may include a shaft portion 132 and a head portion 136. The head portion 136 may be coupled to a first end of the shaft portion 132. The head portion 136 may also include a drive opening 138 positioned on the first end of the head portion 136 opposite the shaft portion 132. The shaft portion 132 may be, for example, a threaded along at least a portion of the shaft 132 and may include a locking opening 134. The locking opening 134 may be positioned, for example, perpendicular to a longitudinal axis of the fastening member 130. As shown in FIGS. 11-20, the shaft portion 132 is threaded from the head portion 136 toward the second end and includes a non-threaded section near the second end of the shaft portion 132. The coupling member 140 may include a through hole 142 extending from a first end of the coupling member 142 the second end. The coupling member 140 may also include a locking opening 144 extending from a side of the coupling member 140 into the through hole 142. The locking opening 144 may be, for example, generally perpendicular to the through hole 142. The locking opening 144 may receive a pin or locking member 146.

The alignment guide 100 may also include a first distal proximal translating member 150 and a second distal proximal translating member 160, as shown in at least FIGS. 11-20. The first translating member 150 may include a body 152 with a first opening or securement opening 154 positioned at a distal end of the body 152. In addition, the first translating member 150 may include a groove 156 positioned around the body 152 between a midpoint of the body 152 and the proximal end of the body 152. The first translating member 150 may also include a plurality of teeth 158 extending along at least a portion of the length of the body 152 from the first end of the second end. The first translating member 150 may also include a plurality of dimension markings 159 positioned along at least a portion of the length of the body 152. The second translating member 160 may include a body 162 with a first opening or securement opening 164 positioned at a distal end of the body 152. In addition, the second translating 160 may include a groove 166 positioned around the body 162 between a midpoint of the body 162 in the proximal end of the body 162. The second translating member 160 may also include a plurality of dimension markings 168 positioned along at least a portion of the length of the body 162.

With continued reference to FIGS. 11-20, the first translation mechanism 110 also includes the coupling member 240. The coupling member 240 includes a base 242, a securement fastener or telescoping rod knob 274 received within the coupling member 240, and a drive member 276 rotatably coupled to the base 242 of the coupling member 240. The base 242 may include a through hole 244 extending into the base 242 from a first side. The base 242 may also include a channel 246 extending into the base 242 from a bottom surface. The channel 246 may include a female dovetail portion or receiving member 248. The receiving member 248 may include a first protrusion 250 positioned on a first side of the bottom surface and a second protrusion 252 positioned on a second side of the bottom surface. The opening of the receiving member 248 at the bottom surface may be, for example, smaller than the width of the interior top surface of the channel 246. For example, the channel 246 may have angled side surfaces as the channel 246 extends into the base 242. In addition, the base 242 may include at least one window 254 extending from the first end into the channel 246 and at least one window 254 extending from the second end into the channel 246. The base 242 may also include a locking pin opening 256 extending from the first end to the second end, for example, between the two windows 254. The base 242 may further include an engagement pin opening 258 extending into the base 242 from the first end.

A locking member or indicator member 260 may extend away from a top surface of the base 242 on the first side, as shown in FIGS. 11-20. The locking member 260 may include a through hole 262 extending from the first side toward the second side of the base 242. In addition, the locking member 260 may include a pointer 264 extending away from a top surface of the locking member 260. The pointer 264 may have, for example, a generally triangular shape or alternative shape which terminates in a point. Finally, the locking member 260 may include a locking pin opening 266 the first end of the second end and positioned near a top surface of the locking member 260. The locking pin opening 266 may extend through the locking member 260, for example, perpendicular or generally perpendicular to the through hole 262. A translating protrusion 270 may also extend away from a top surface of the base 242 adjacent to the locking member 260. The translating protrusion 270 may include a through hole or threaded hole 272 extending between the first end and the second end. The locking member 260 may be spaced apart from the translating protrusion 270 to form a channel and the channel may be, for example, sized and shaped or configured to receive a side of the housing 112.

The securement fastener 274 may include, for example, a head portion with a drive feature and a shaft portion extending away from a second end of the head portion. The shaft portion may be, for example, threaded along at least a portion of its length. The drive member 276 may include a shaft 278 is a groove 280. The groove 280 may be, for example, inset into the shaft 278 and may extend around a portion of the circumference of the shaft 278. The drive member 276 may also include a drive shaft 282 with a drive opening 284 at a first end of the drive member 276. The drive shaft 282 may have, for example, a diameter smaller than the diameter of the shaft 278. In addition, the head portion 286 may be coupled to the second end of the drive member 276 and there may be a groove 288 positioned between shaft 270 and the head portion 286. The drive member 276 may further include a locking pin opening 290 extending through the drive member 276 and positioned within the groove 288.

With continued reference to FIGS. 11-20, the second translation mechanism, distal proximal adjustment member, or gearbox 170 may include a housing 172, a coupling fastener or internal external adjustment screw 202, locking fastener 204, a drive member 212, an engagement member 218, and a locking cap 226. The housing 172 may include a base 174 with a first extension member or proximal extension member 190 extending away from a top surface of the base 174 and a second extension member or distal extension member 200 extending away from a bottom surface of the base 174. The base 174 may include a fastener hole 176 positioned near the second end of the housing 172 and a fastener hole or locking hole 192 extending at least partially through the first extension member 190 from a first side into the coupling recess 196. The base 174 may also include a locking pin hole 178 positioned between the fastener hole 136 and the locking hole 192. The base 174 may further include a through hole or alignment pin hole 180 extending through the base 174 from a first side to a second side. The through hole 180 may have, for example, an oval or elliptical shape. The through hole 180 may be positioned below the fastener hole 192. The base 174 may also include a tool opening 182 positioned near the first end of the base 174. A locking cap opening 184 may extend into the base 174 from a second side and engage or overlap with the tool opening 182. The locking cap opening 184 may have, for example, a diameter larger than the diameter of the tool opening 182. The locking cap opening 184 may be, for example, threaded to receive a fastener 202. The housing 172 may also include the cavity 186 positioned within the base 174. The housing 172 may also include an enlarged opening or keyhole portion 188 positioned on a top surface of the base 174. The enlarged opening 188 may extend from the top surface of the base 174 into the cavity 186. In addition the locking cap opening 184 may extend from a second end of the base 174 into the cavity 186.

As shown in at least FIGS. 11, 12, 19 and 20, the housing 172 may also include a locking pin hole 194 extending through the first extension member 190 and a medial lateral direction from a first end toward the second end. The first extension member 190 may also include a coupling hole 196 extending into the first extension member 190 from a top surface. The coupling hole 196 may be, for example, a circular or around recess or alternative shaped recess corresponding to the shape of the stem 356 of the third translation mechanism 300. In addition, the first extension member 190 may also include two threaded recesses 198 positioned on opposite sides of the coupling hole 196. The threaded recesses 198 may be configured or sized and shaped to receive a first alignment pin 206 and a second alignment pin 208. The alignment tends 206, 208 when inserted may have a portion of the pins 206, 208 extending above a top surface of the first extension member 190 to engage a bottom surface of an adjustment housing 340 of the third translation mechanism 300. The second extension member or distal extension member 200 may extend between the first end and the second end of the base member 174. In addition, the cavity 186 may extend through the base 174 as well as the second extension member 200 from a top surface to a bottom surface of the housing 172. The cavity 186 may be positioned near a first end of the housing 172. The housing 172 may also include a through hole 187 positioned near a second end of the housing 172. The through hole 187 may extend through the base 174 as well as the second extension member 200 from a top surface to a bottom surface of the housing 172. The cavity 186 and the through hole 187 may be configured or sized and shaped to receive the first translating member 150 and the second translating member 160, respectively.

The second translation mechanism 170 may also include a coupling fastener or internal external adjustment screw 202 for engagement with the fastener hole 192 of the housing 172, as shown in at least FIGS. 11-20. In addition, the second translation mechanism 170 may include a locking fastener 204 received within the fastener hole 136. The fastener hole 136 extends into the through hole 187 to enable the locking fastener 204 to engage the second translating member 160 and secure the second translating member 160 at a desired height. The second translation mechanism 170 may also include a drive member 212 with a first portion including a drive opening 214 at a first end and a driveshaft 216 extending away from the first portion to the second end. The driveshaft 216 may engage or be received within a through hole 224 of an engagement member 218. The engagement member 218 may also include a body or shaft 220 and a plurality of teeth 222 extending around the circumference of the exterior surface of the body 220. The plurality of teeth 222 may extend along only a portion of the length of the body 220. The plurality of teeth 222 may be configured or sized and shaped to engage the plurality of teeth 158 of the first translating member 150. The through hole 224 may extend through the body 220 along the entire length of the engagement member 218. The driveshaft 216 may extend completely through the through hole 224 to engage the locking cap 226. For example, the locking cap 226 may engage or interface with the engagement member 218 to secure the drive member 216 in a locked position. Although not shown, a washer may be positioned between the engagement member 218 and the locking cap 226 when assembled with the drive member 212. The locking cap 226 may include a body 228 and a through hole 230 extending through the body 228 from the first end to a second end. The locking cap 226 may also include recesses or drive features 232 inset into the first end and the second end of the body 228. Further, the locking cap 226 may include threads 234 along the exterior circumference between the first end and the second end of the body 228. The threads 234 may be configured or sized and shaped to engage the locking cap opening 184.

Figure 9:
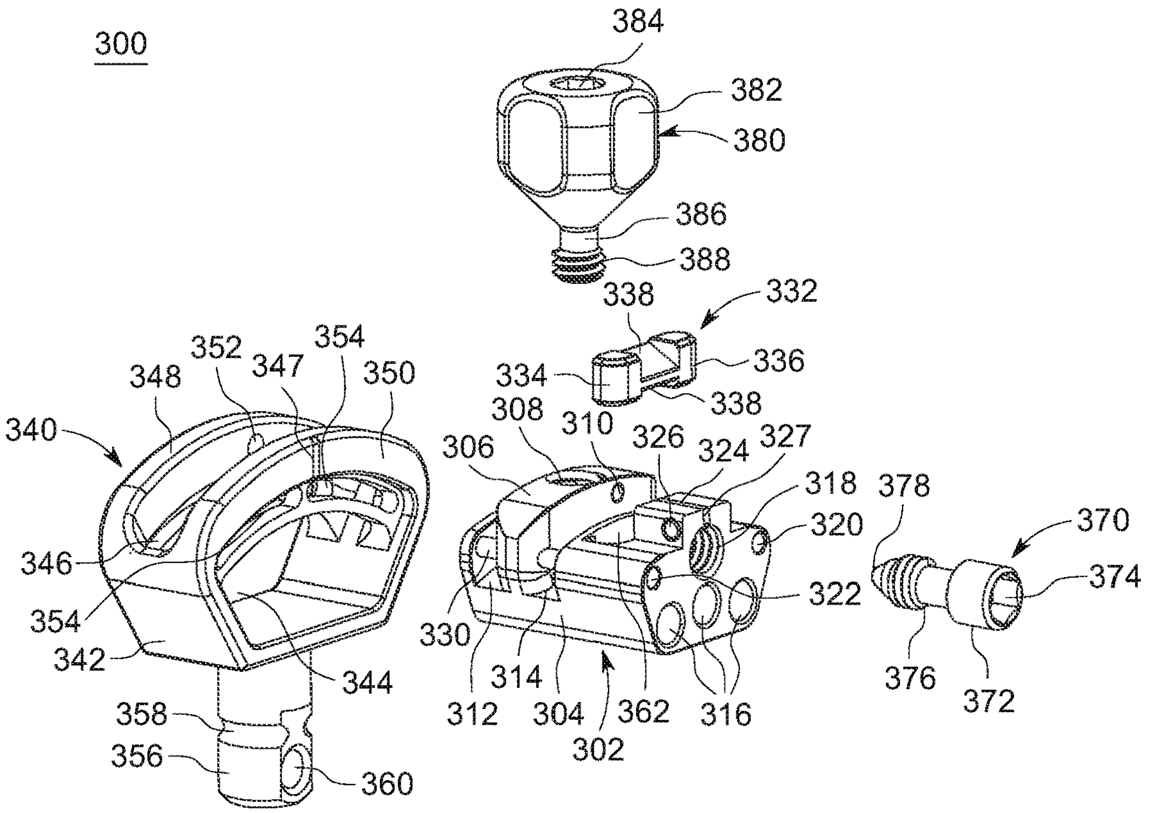
FIG. 9 is an exploded, first perspective view of the third translation mechanism of the alignment guide of FIG. 1, in accordance with an aspect of the present disclosure.
Figure 10:
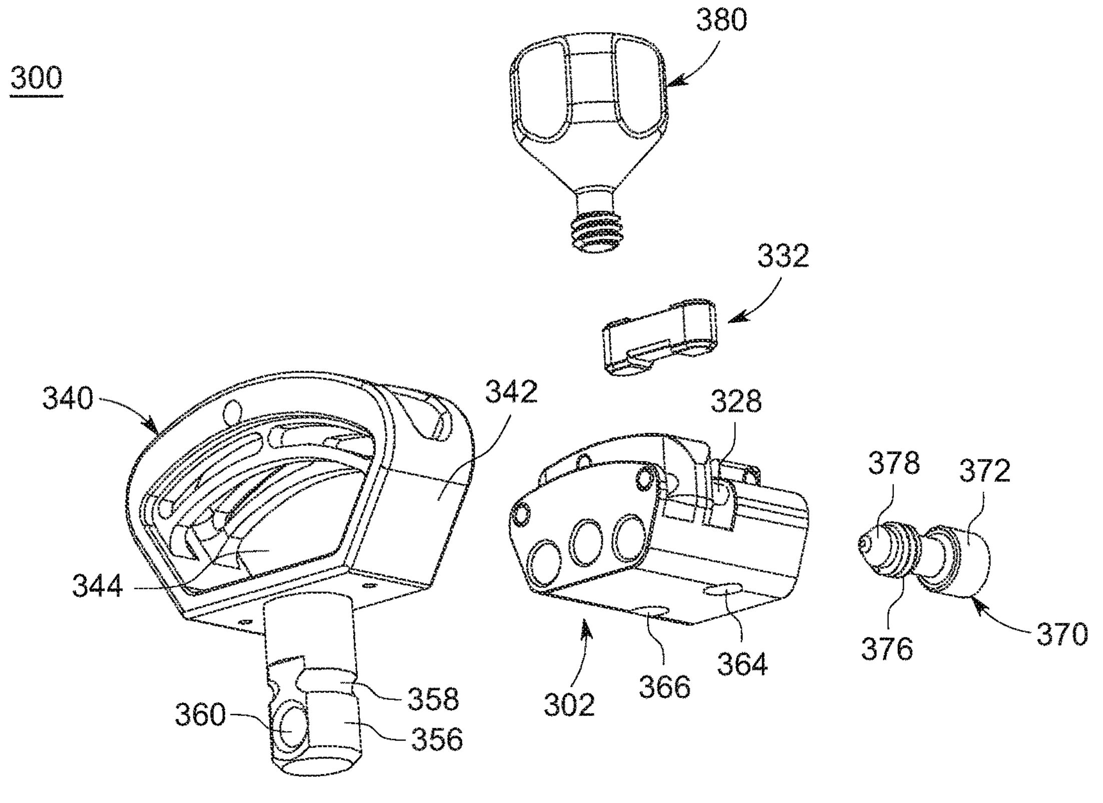
FIG. 10 is an exploded, second perspective view of the third translation mechanism of FIG. 9, in accordance with an aspect of the present disclosure.
Figure 11:
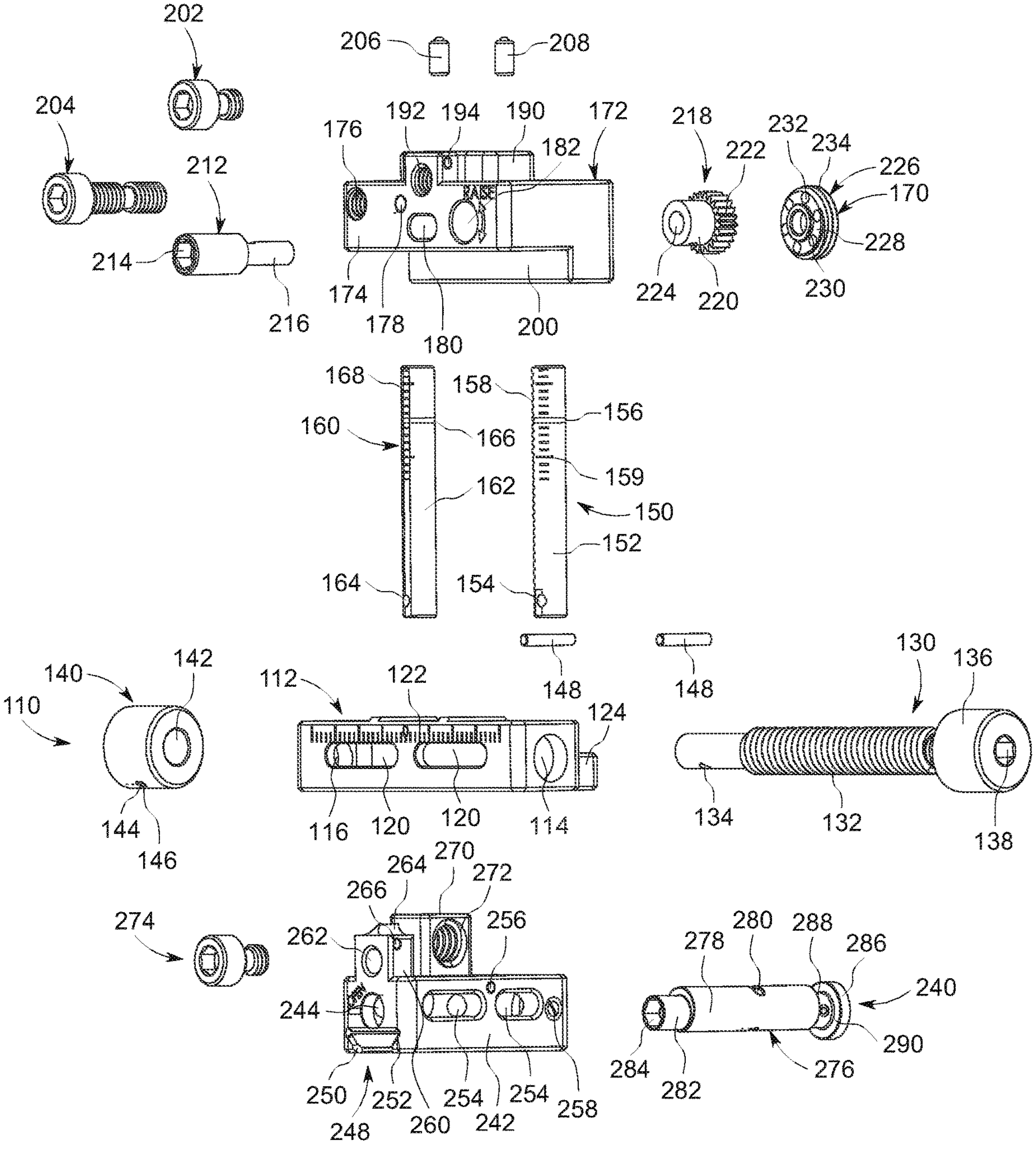
FIG. 11 is an exploded, first perspective view of the first and second translation mechanisms of the alignment guide of FIG. 1, in accordance with an aspect of the present disclosure.
Figure 12:
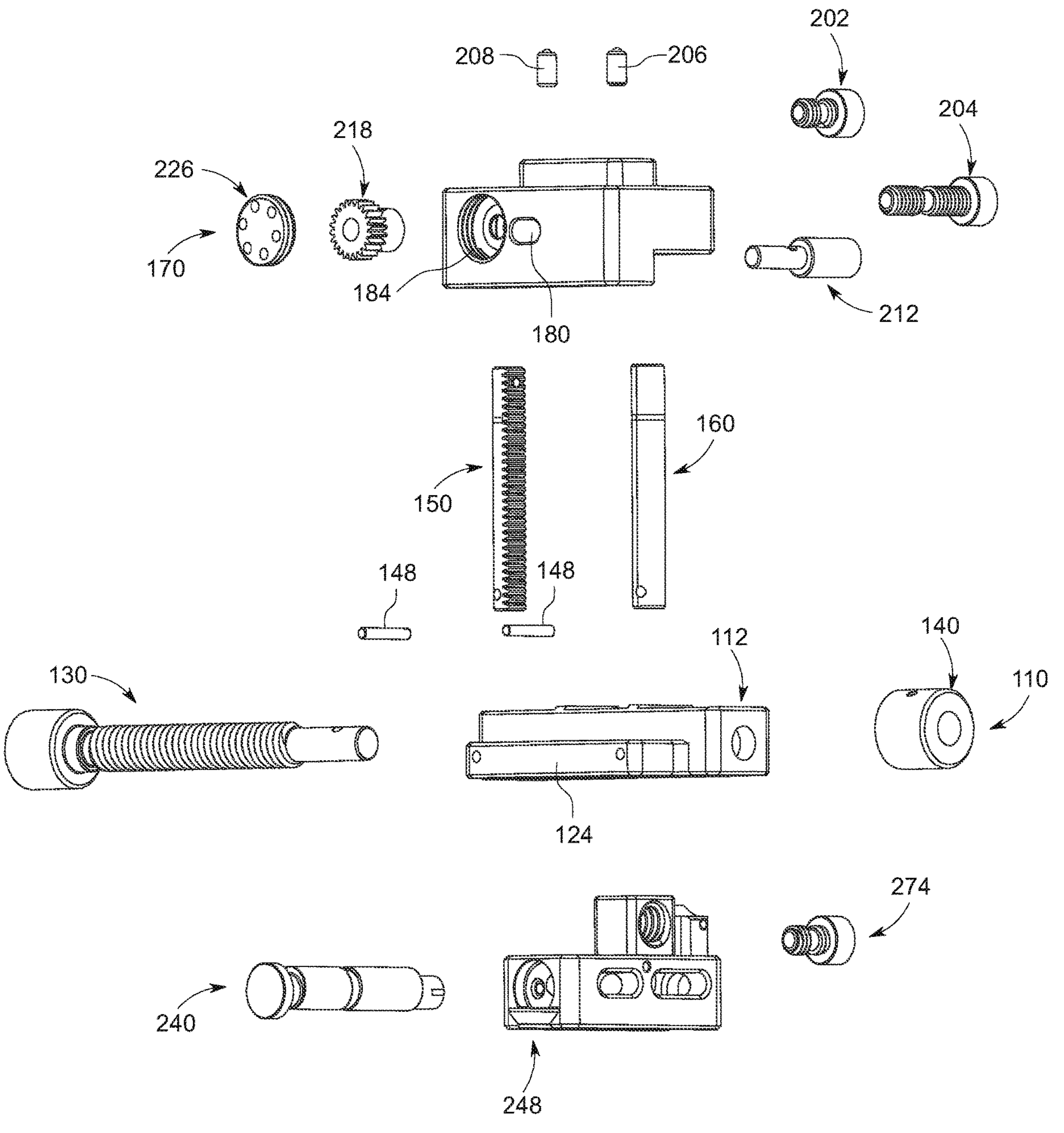
FIG. 12 is an exploded, second perspective view of the first and second translation mechanisms of FIG. 11, in accordance with an aspect of the present disclosure.
Figure 13:
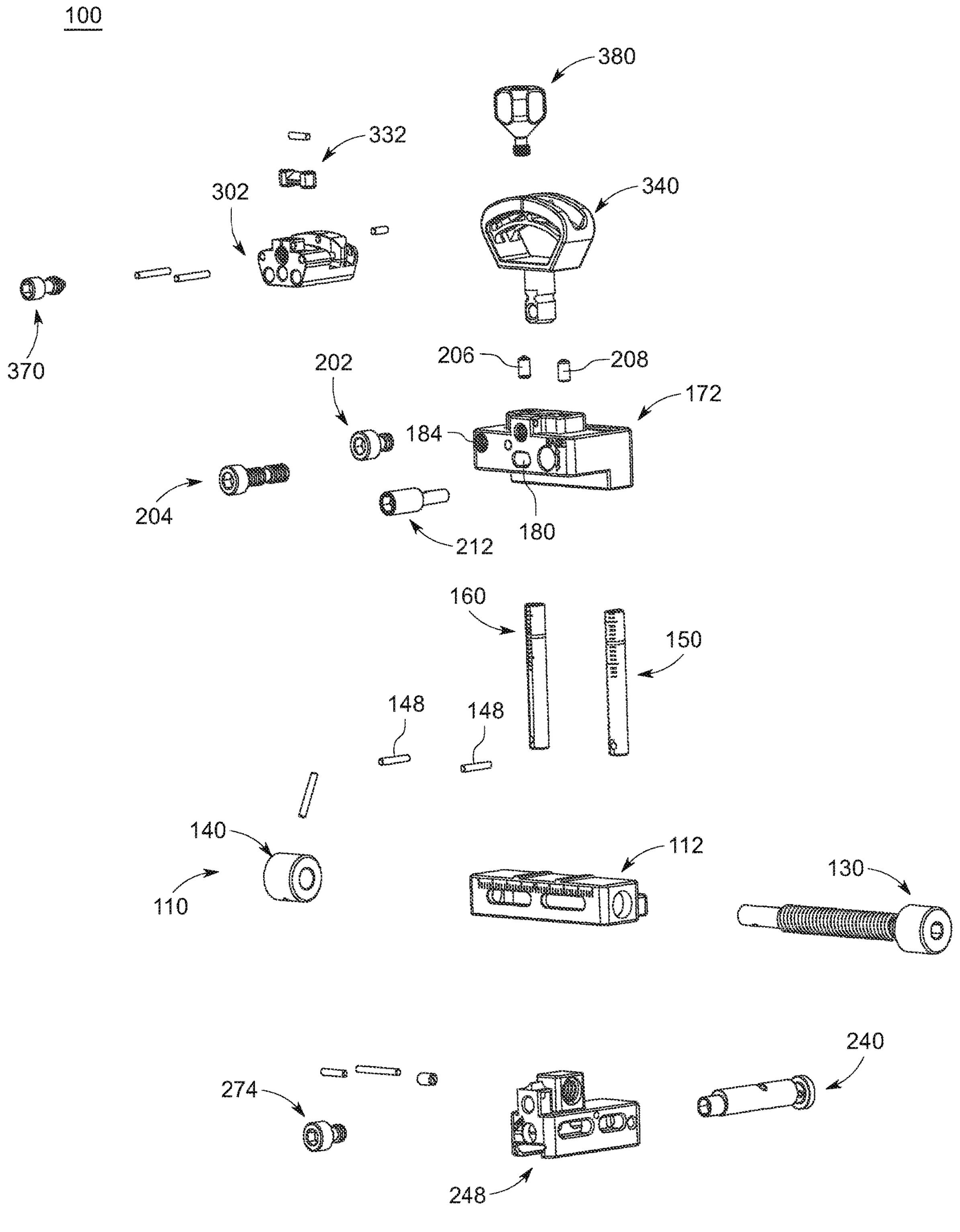
FIG. 13 is an exploded, first perspective view of the alignment guide of FIG. 1, in accordance with an aspect of the present disclosure.
Figure 14:
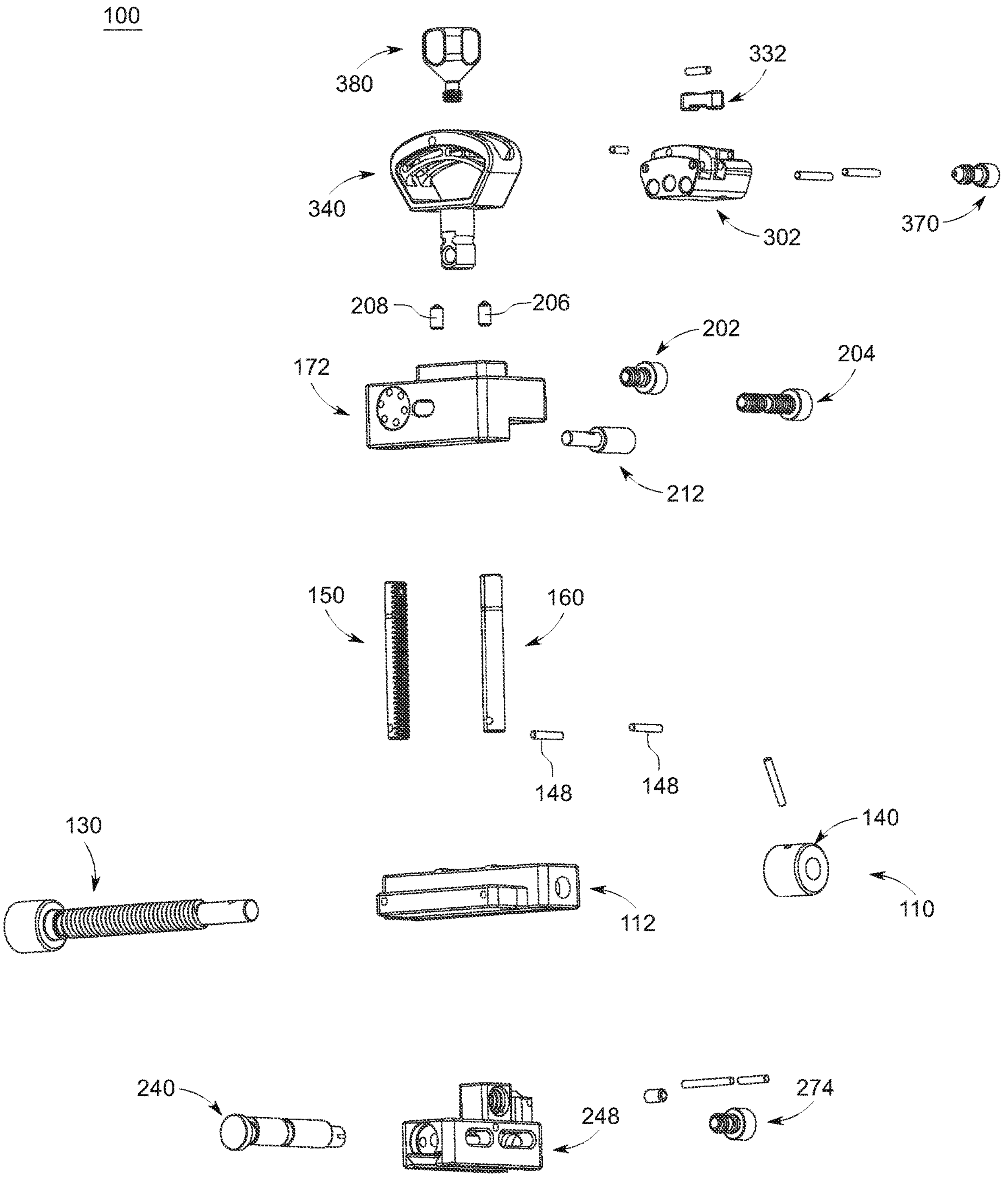
FIG. 14 is an exploded, second perspective view of the alignment guide of FIG. 1, in accordance with an aspect of the present disclosure.
Figure 15:
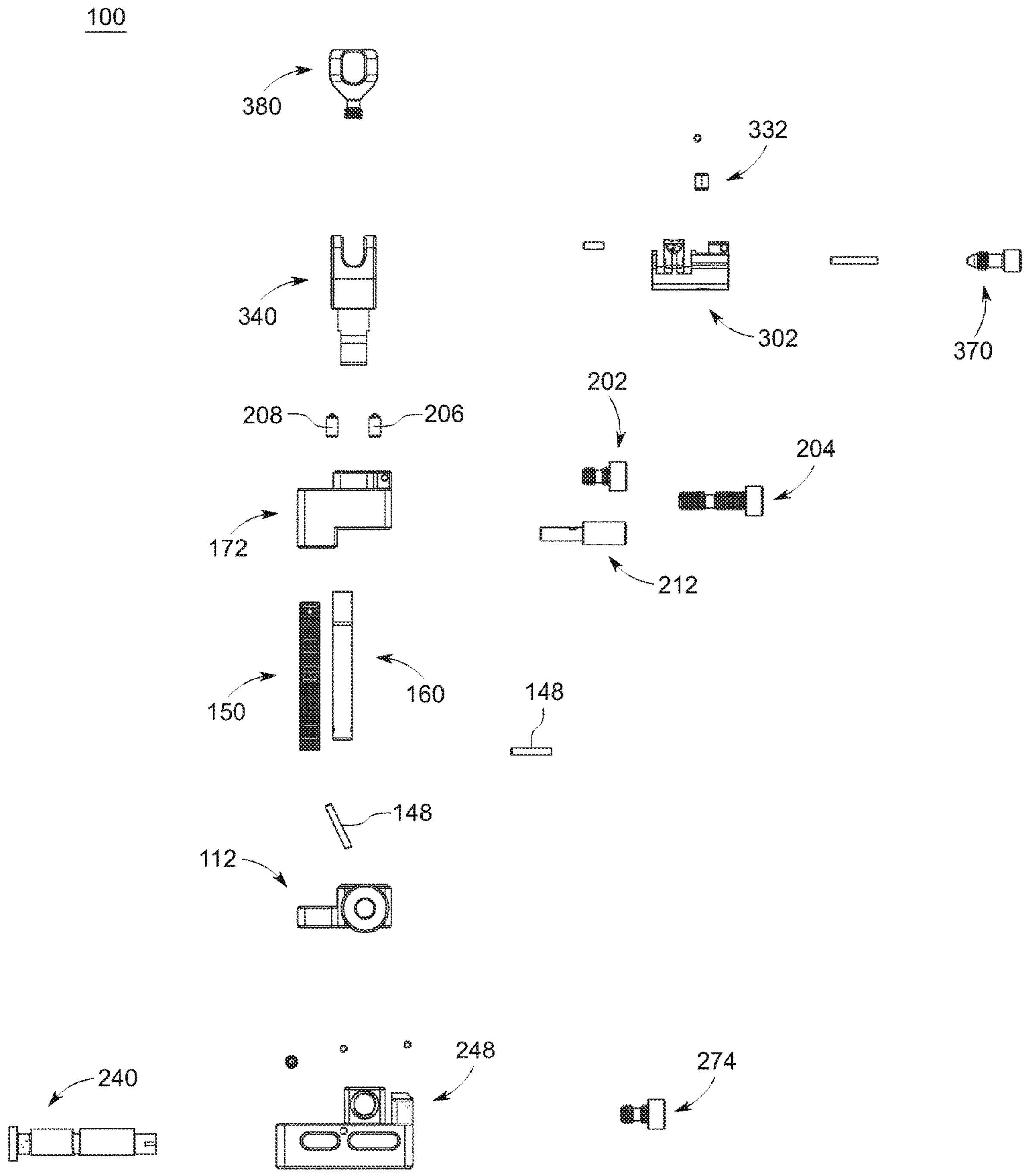
FIG. 15 is an exploded, first end view of the alignment guide of FIG. 1, in accordance with an aspect of the present disclosure.
Figure 16:
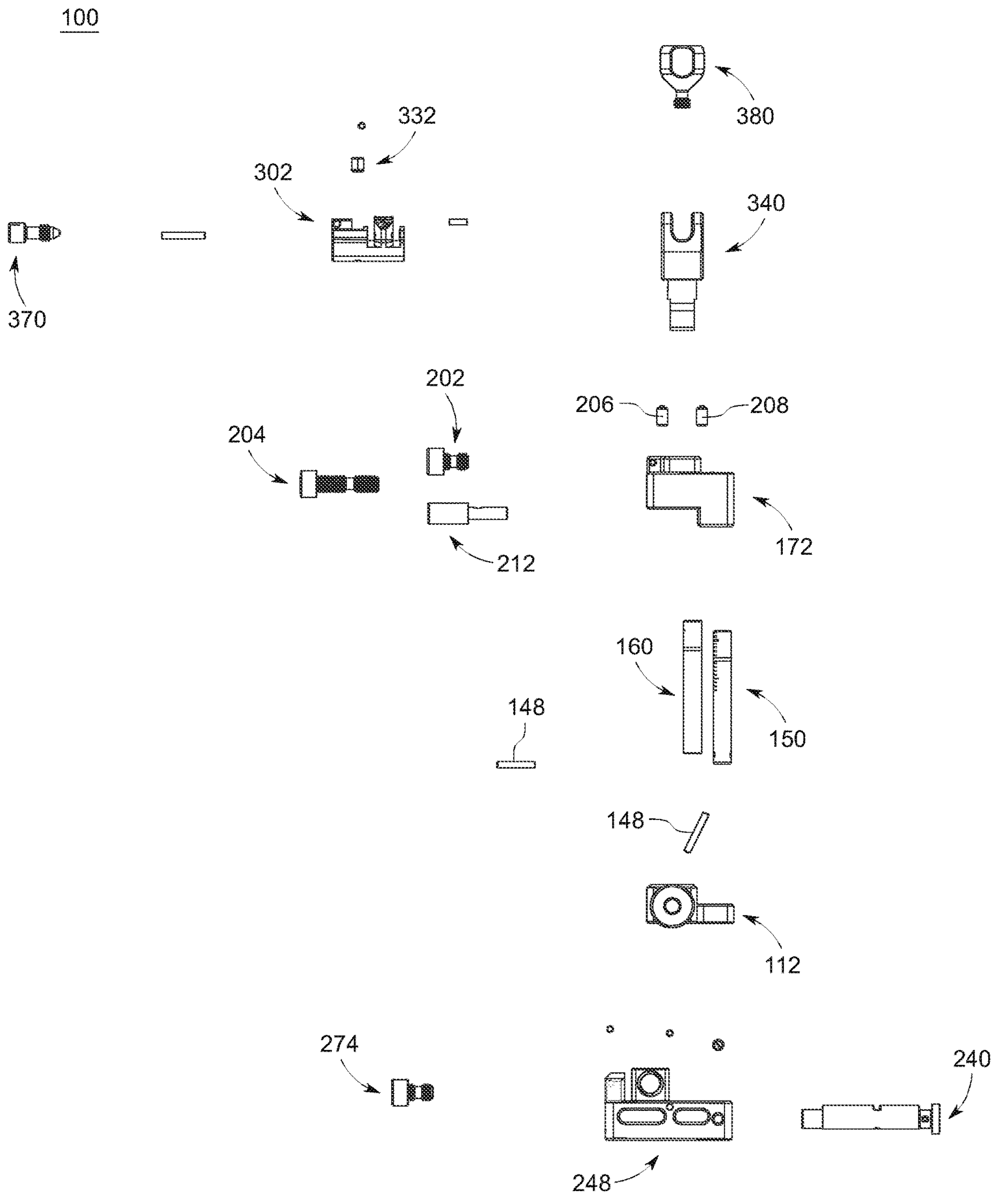
FIG. 16 is an exploded, second end view of the alignment guide of FIG. 1, in accordance with an aspect of the present disclosure.
Figure 17:
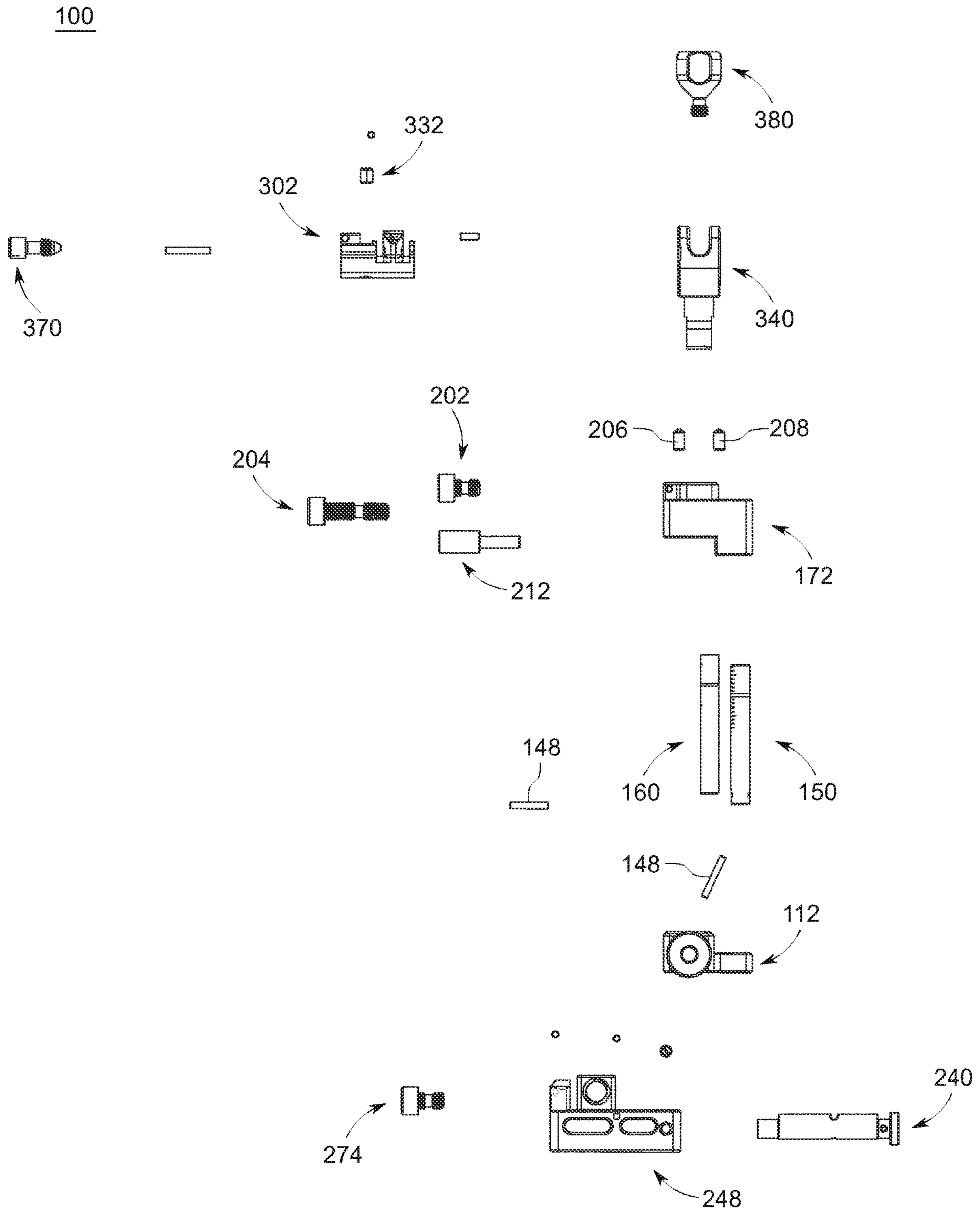
FIG. 17 is an exploded, first side view of the alignment guide of FIG. 1, in accordance with an aspect of the present disclosure.
Figure 18:
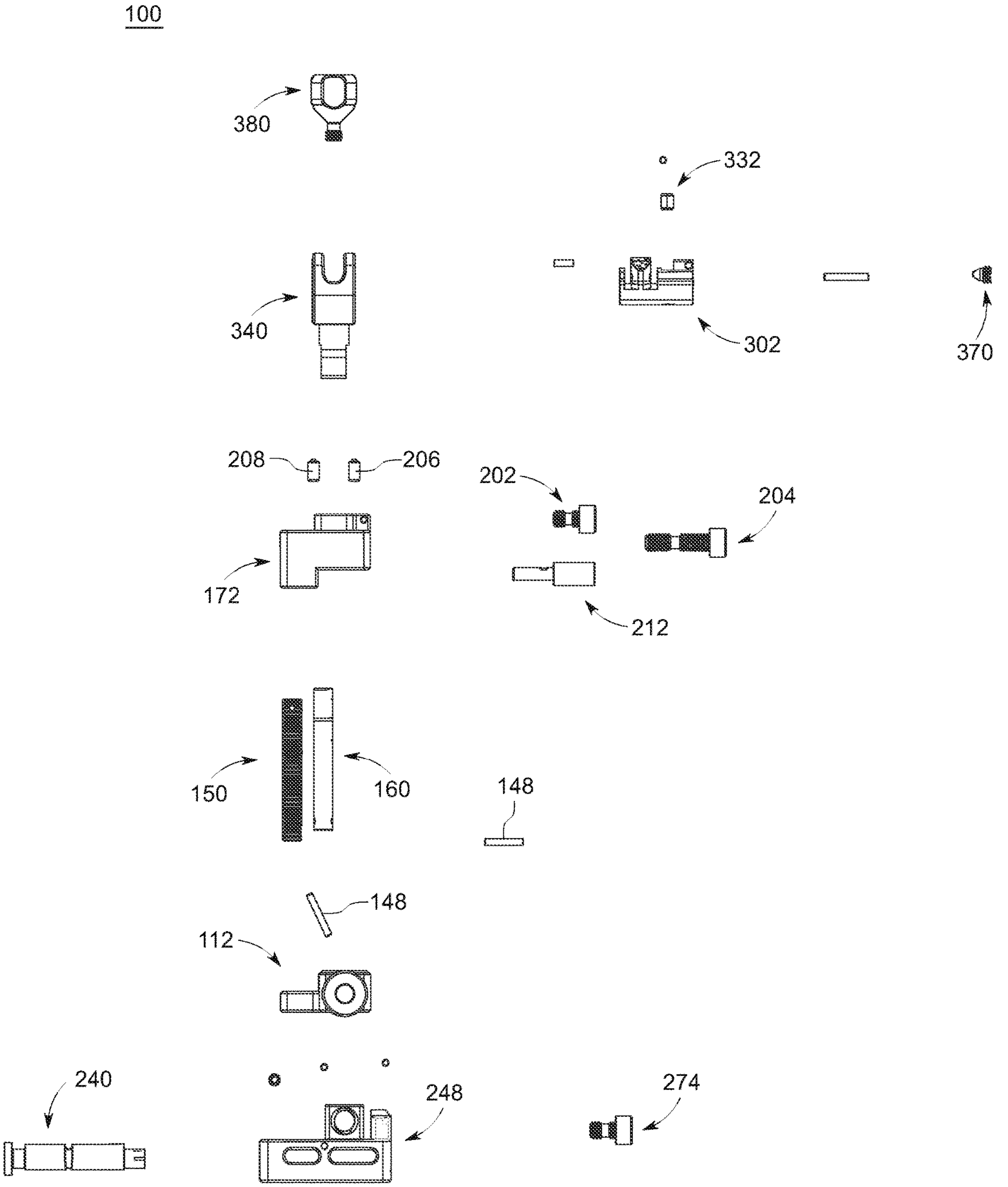
FIG. 18 is an exploded, second side view of the alignment guide of FIG. 1, in accordance with an aspect of the present disclosure.

Referring now to FIGS. 9 and 10 and with continued reference to FIGS. 11-20, a third translation mechanism or varus-valgus adjustment member 300 is shown. The third translation mechanism 300 may include a translating member 302, an adjustment housing 340 which receives the translating member 302, a fastener or locking knob 370 rotatably coupled to the translating member 302, and a locking member or locking knob 380 for coupling the adjustment housing 340 to the translating member 302. The translating member 302 may include a body 304 with a first protrusion 306 positioned near a second side of the body 304. The first protrusion 306 may include a first channel 312 positioned on a first side and a second channel 314 positioned on a second side. The first protrusion 306 may also include a threaded opening 308 for receiving the locking knob 380. The threaded opening 308 may extend into the first protrusion 306 from a top surface. The first protrusion 306 may also include a locking pin opening 310 extending through the first protrusion 306 from the first side to the second side and overlapping with the threaded opening 308. The opening 310 may receive a locking pin (not shown). The translating member 302 may also include at least one through hole or alignment pin hole 316 extending from a first side to a second side of the body 304. The at least one through hole 316 may be configured or sized and shaped to receive a wire, pin, or the like for holding instruments on a patient's bone during a TAR procedure. As shown, the at least one through hole 316 may be, for example, three through holes 316. The translating member 302 may also include a threaded hole or locking hole 318 extending into the body 304 from a first side toward the second side. The translating member 302 may also include a first locking pin opening 320 and a second locking pin opening 322. The first locking pin opening 320 may extend from a first side through to a second side of the body 304 and may receive a first locking pin 328. The second locking pin opening 322 they extend from the first side through the second side of the body 304 and may receive a second locking pin 330. The translating member 302 may also include a second protrusion 324 extending away from a top surface of the body 304 at a first side. The second protrusion 324 may include a locking pin opening 326 extending through the second protrusion 324 from the first end to a second end perpendicular to the threaded hole 318. In addition the second protrusion 324 may include an alignment marking 327. The alignment marking 327 may be used, for example, to align the translating member 302 and the center position within the adjustment housing 340. The adjustment housing 340 may include an alignment marking 347 to designate, for example, the center of the adjustment housing 340. The translating member 302 may also include an opening 362 positioned between the second channel 314 and the second protrusion 324. The opening 362 may be, for example, an elongated opening extending from a top surface of the body 304 toward the bottom surface. In addition, translating member 302 may include a first through hole 364 positioned on a first end of the body 304 and extending from a bottom of the opening 362 to a bottom of the body 304. The translating member 302 may further include a second through hole 366 positioned on a second end of the body 304 and extending from a bottom of the opening 362 to a bottom of the body 304.

As shown in FIGS. 9 and 10, the adjustment housing 340 may include a body 342 with a through hole 344 extending from a first side to a second side. The adjustment housing 340 may also include a channel 346 extending from a top surface of the body 342 into the through hole 344. The through hole 344 may include, for example, a bottom surface, two side surfaces extending away from the bottom surface at opposing angles, and a curved upper surface. The body 342 may also include a first arm member 348 and a second arm member 350 positioned on each side of the channel 346. The arm members 348, 350 may be, for example, arced or curved between the first end and the second end of the adjustment housing 340. The arm member 348 may also include a locking pin opening 352 for receiving a locking pin (not shown) to engage a portion of the shaft 386 of the locking member 382 and retain the locking member 380 within the channel 346 whether in a locked or unlocked position. The adjustment housing 340 may also include recess slots 354 extending through a lower portion of each arm member 348, 350. As shown, the recess slots 354 may be, for example, to recess slots 354 below each arm member 340, 350. The adjustment housing 340 may also include a stem or coupling stem 356 extending away from a bottom surface of the body 342. The stem 356 may include a groove 358 extending around at least a portion of the circumference of the stem 356. The groove 358 may be, for example, configured or sized and shaped to engage a locking pin (not shown). The stem 356 may also include a through hole 360 extending through the stem 356 from the first side to a second side. The through hole 360 may be, for example, configured or sized and shaped to receive a coupling fastener

202 of the second translation mechanism 170 to couple the third translation mechanism 300 to the second translation mechanism 170.

With continued reference to FIGS. 9 and 10, the third translation mechanism 300 may also include a securement member or securement block 332 configured or sized and shaped to be received within the opening 360 to the body 304 of the translating member 302. The securement block 332 may include a first end 334 and a second end 336. The securement block 332 may also include a tapered regions or tapered surfaces 338 positioned between the first end 334 and the second end 336. The tapered regions 338 may form, for example, a wedge-shaped. As shown, the tapered region 338 may include a first taper on the top surface and a second taper on the bottom surface. The tapered surface 338 may be, for example, configured or sized and shaped to engage the fastener 370.

The fastener or varus-valgus locking knob 370 may include a head 372 at a first end and a shaft 376 extending away from the second end of the head 372 to the second end. The fastener 370 may also include a drive feature 374 recessed in the first end of the head 372. In addition, the fastener 370 may be threaded along at least a portion of the length of the shaft 376. The shaft 376 may also include an engagement tip 378 at the second end. The engagement tip 378 may be, for example, pointed or tapered to engage the tapered surface 338 of the securement block 332.

The locking member or varus-valgus locking knob 380 may include a head portion 382 and a shaft 386, as shown in FIGS. 9 and 10. The head portion 382 may have a larger diameter than the shaft portion 386 and may include at least one planar surface around the circumference of the head portion 382. The head portion 382 may also include a drive feature 384 recessed into a first end of the head portion 382. The shaft 386 may extend away from a second end of the head portion 382 opposite the drive feature 384 and may include a threaded portion 388 along at least a portion of the shaft 386. The threaded portion 388 may be, for example, configured or sized and shaped to be received within or engage the threaded opening 308 and the first protrusion 306 of the translating member 302.

The first translation mechanism 110 may be assembled by, for example, inserting the translating protrusion 270 into the channel 246 of the base 242. The securement fastener 274 may be inserted through, for example, the through hole 262 to engage the first side of the housing 112. In addition, the drive member 276 may be inserted into the through hole 244 and an engagement pin (not shown) may be inserted through the engagement pin hole 258 until the engagement pin engages the groove 288 in the drive member 276. Then, the fastening member 130 may be inserted into the first opening 114, through the cavity 118 and the through hole 272 of the translating protrusion 270, and a portion of the fastening member 130 may extend out of the second opening 116. The through hole 142 of the coupling member 140 may receive the portion of the fastening member 130 extending out of the second opening 116. In addition, a pin 146 may be inserted into the locking opening 144 of the coupling member 140 and through the locking opening 134 of the fastening member 130 to retain the threaded portion of the shaft portion 132 within the cavity 118 of the housing 112.

Next, a distal end of the first translating member 150 may be inserted into the first recess 126 and a locking pin or locking member 148 may be inserted through the extension member 124 and the first opening 154 to secure the first translating member 150 to the extension member 124 of the housing 112. The distal end of the second translating member 160 may be inserted into the second recess 128 and a locking pin 148 may be inserted through the extension member 124 and second opening 164 to secure the first translating member 160 to the extension member 124 of the housing 112. Then, the second translation mechanism 170 may be aligned with and slid onto the translating members 150, 160. The first translating member 150 may be received within the cavity 186 of the housing 172 and a plurality of teeth 158 may engage the plurality of teeth 222 of the engagement member 218 to allow for the housing 172 to translate with respect to the coupled first translation mechanism 110 and coupling member 240. The engagement member 218 will be positioned within the cavity 186. The drive member 212 will be coupled to the engagement member 218 to allow for rotation of the drive member 212 from a first side to be translated to rotation of the engagement member 218. The locking cap 226 may also be inserted into the locking cap opening 184 to engage the second end of the drive member 212 and retain the engagement member 218 within the cavity 186. For example, the locking cap 226 may engage or interface with the engagement member 218 to secure the drive member 216 in a locked position. Further, the second translating member 160 may be inserted into the through hole 187 when the locking fastener 204 is positioned in an unlocked or first position. In use the locking fastener 204 may be moved to secure the second translating member 160 when the desired proximal distal position is achieved in a locked or second position.

The third translation mechanism 300 may then be secured to the housing 172 of the second translation mechanism 170 by inserting the alignment pins 206, 208 into the threaded recesses 198 and inserting coupling stem 356 of the adjustment housing 340 into the coupling hole 196 of the housing 172. The coupling fastener 202 may be inserted through fastener hole 192 and the housing 172 to engage the through hole 360 in the stem 356 of the adjustment housing 340. A locking pin may further be inserted through the hole 194 and the housing 172 to retain the coupling fastener 202 within the fastener hole 192 in both unengaged and unengaged position. The translating member 302 may then be coupled to the adjustment housing 340 by inserting the translating member 302 into the through hole 344 and aligning the first protrusion 306 with the channel 346. The first arm member 348 and second arm member 350 of the adjustment housing 340 may be received within the first channel 312 and the second channel 314, respectively. Locking pins 328, 330 may be inserted through the holes 320, 322 of the translating member 302 as well as through the recessed slots 354 and the adjustment housing 340 to couple the translating member 302 to the adjustment housing 340. When in an unlocked position the locking fins 328, 330 of the translating member 302 may slide along the recessed slots 354. Once the desired varus-valgus position is achieved the translating member 302 may be locked to the adjustment housing 340 by the fastener 370 and the locking member 380.

Figure 21:
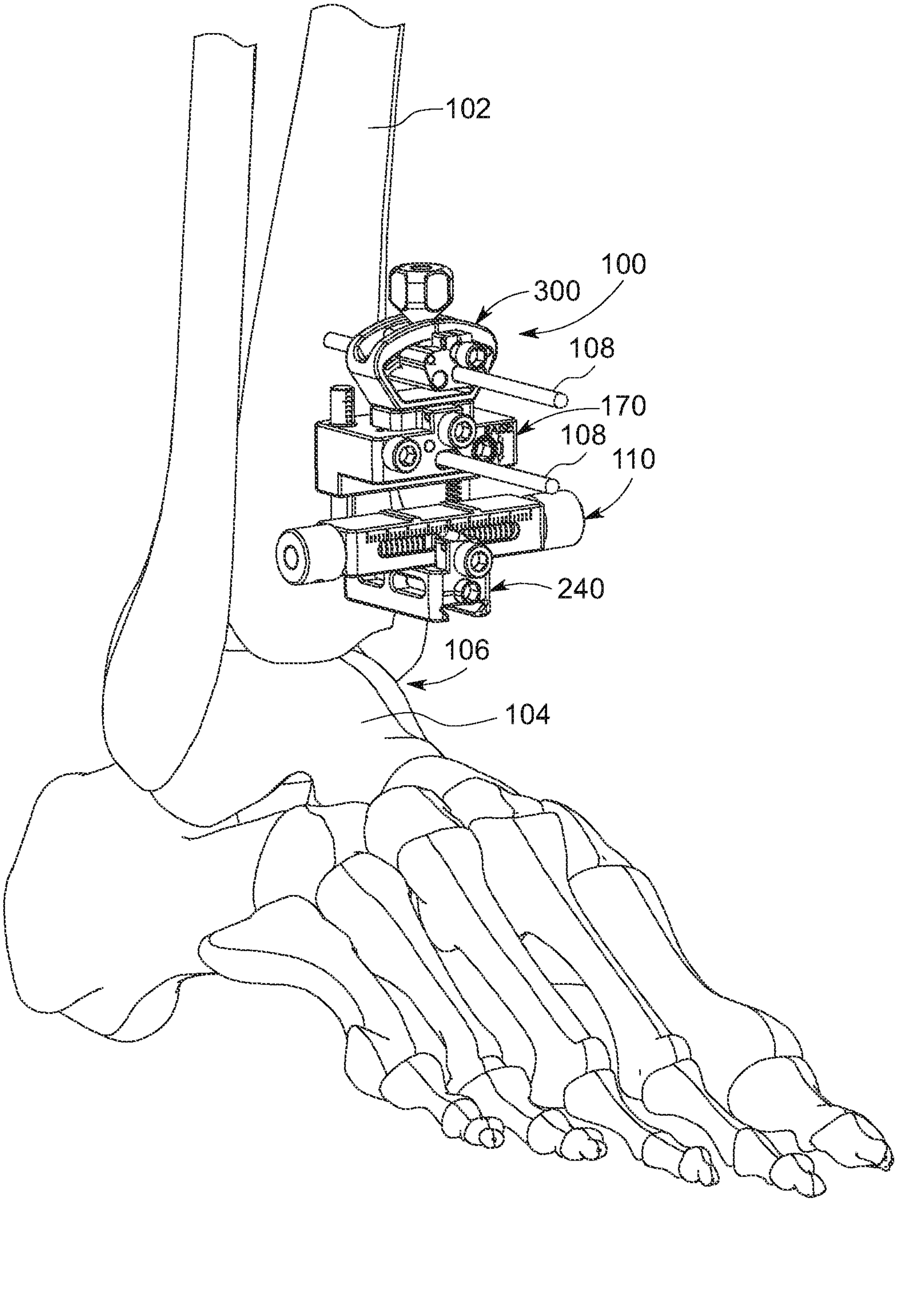
FIG. 21 is a perspective view of the alignment guide of FIG. 1 positioned on a patient's tibia, in accordance with an aspect of the present disclosure.
Figure 22:
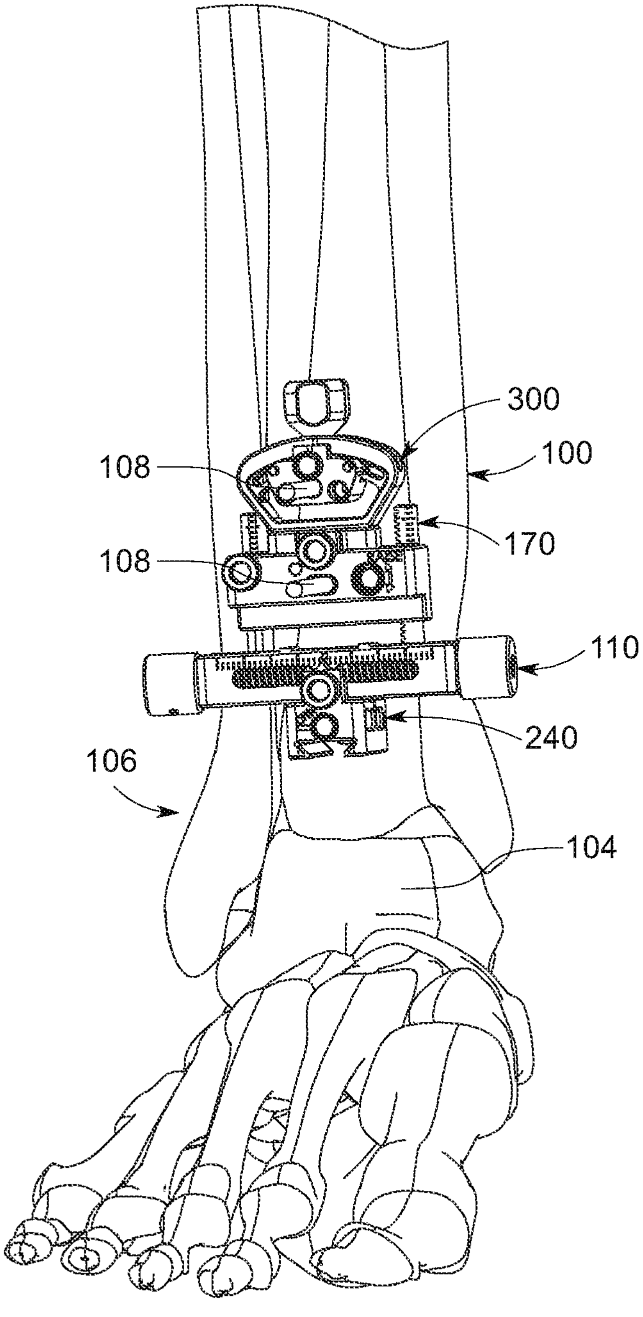
FIG. 22 is a front view of FIG. 21, in accordance with an aspect of the present disclosure.
Figure 23:
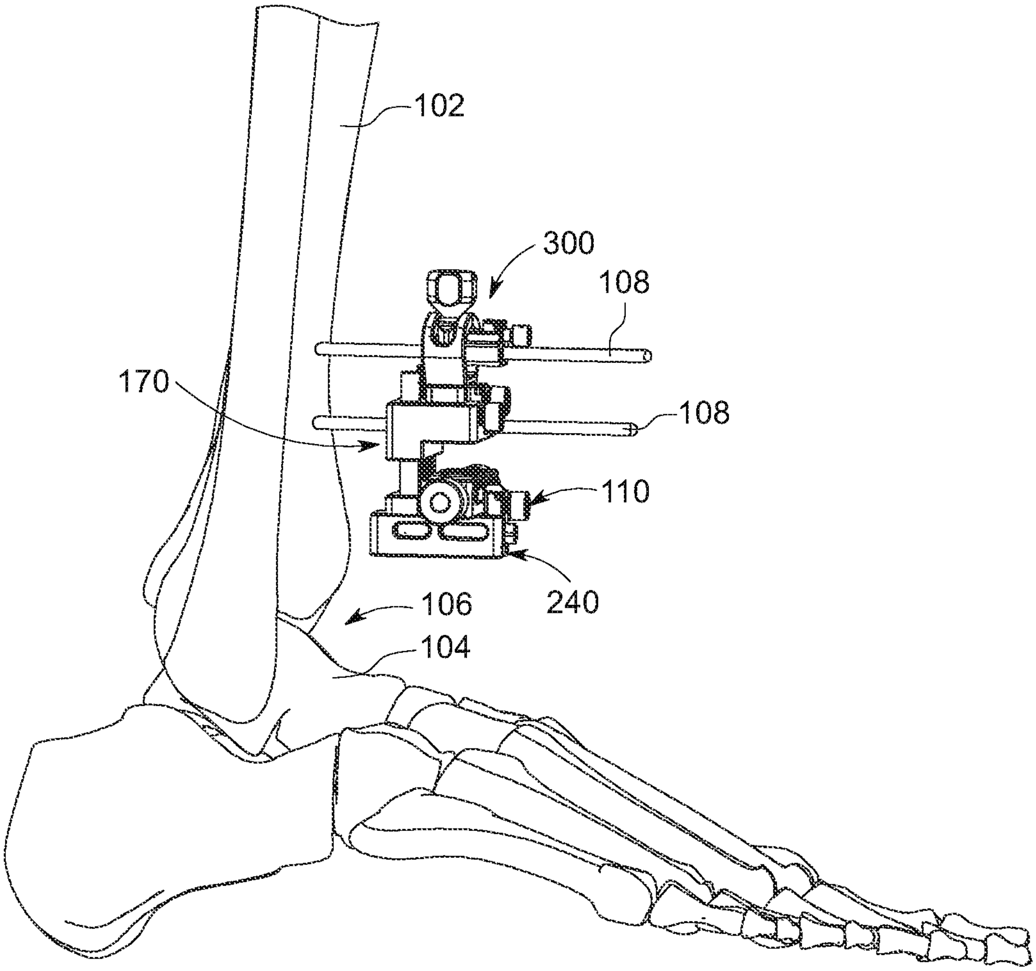
FIG. 23 is a side view of FIG. 21, in accordance with an aspect of the present disclosure.

Referring now to FIGS. 21-23, the alignment guide 100 is positioned on a patient's tibia 102 with two pins 108 and aligned with the ankle joint 106 to allow for a TAR procedure to be performed on the tibia 102 and the talus 104. Once positioned on the tibia 102, the first translation mechanism 110 may be used to achieve medial-lateral adjustment, the second translation mechanism 170 may be used to achieve distal-proximal adjustment, and the third translation mechanism 300 may be used to achieve varus-valgus adjustment. The surgical method may be as described in greater detail in U.S. Provisional Application No. 62/899,460, entitled Total Ankle Replacement Surgical Method, which is hereby incorporated by reference in its entirety.

Figure 25:
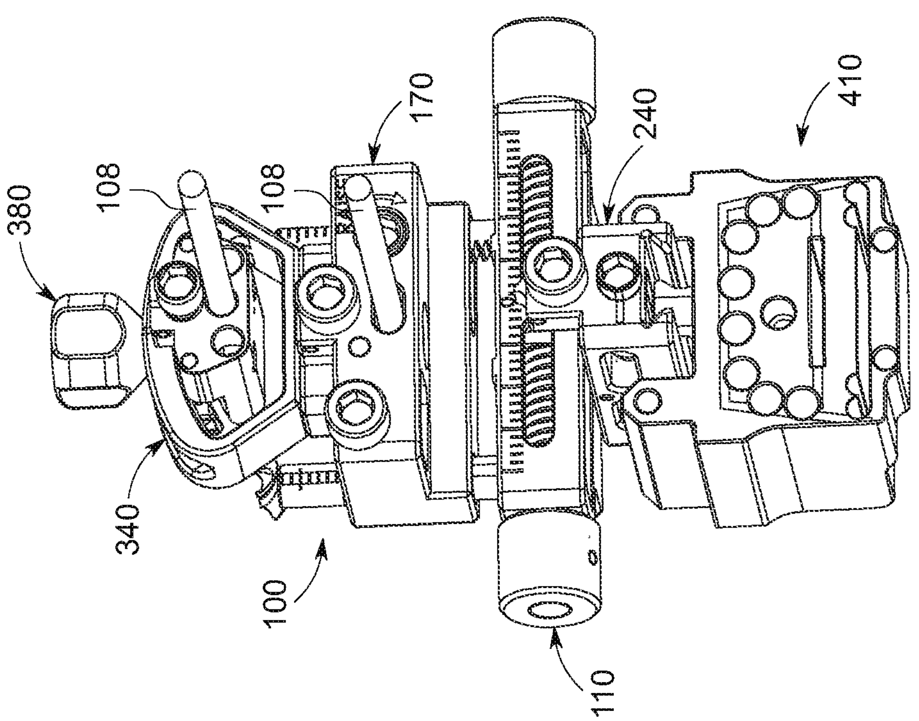
FIG. 25 is a first perspective view of the alignment guide of FIG. 1 with a resection guide coupled to the alignment guide, in accordance with an aspect of the present disclosure.
Figure 24:
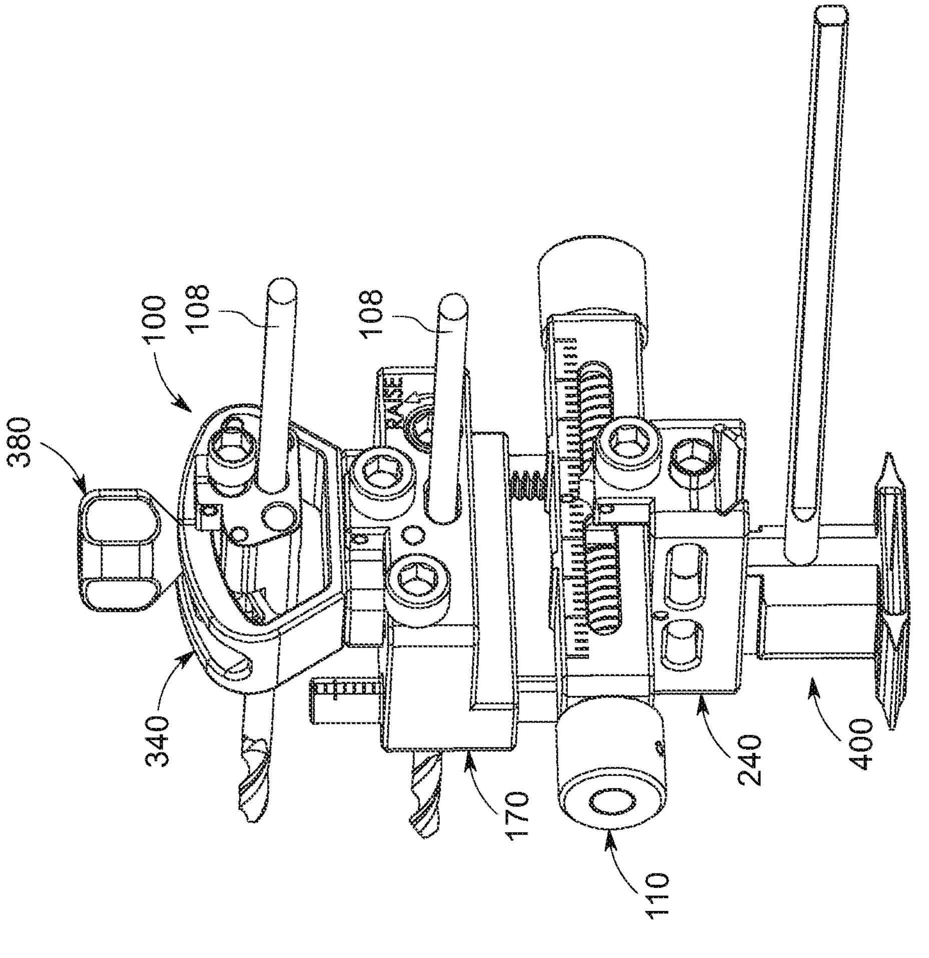
FIG. 24 is a first perspective view of the alignment guide of FIG. 1 with a joint line pointer coupled to the alignment guide, in accordance with an aspect of the present disclosure.
Figure 27:
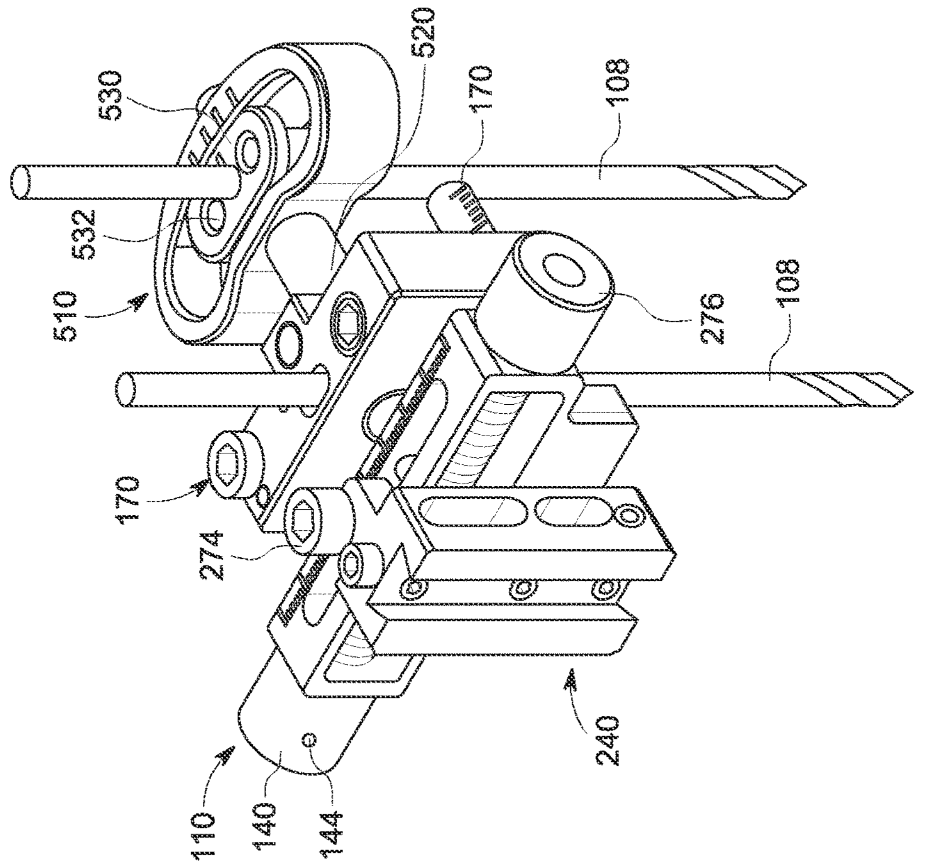
FIG. 27 is a perspective view of the fast track alignment guide of FIG. 1, in accordance with an aspect of the present disclosure.
Figure 26:
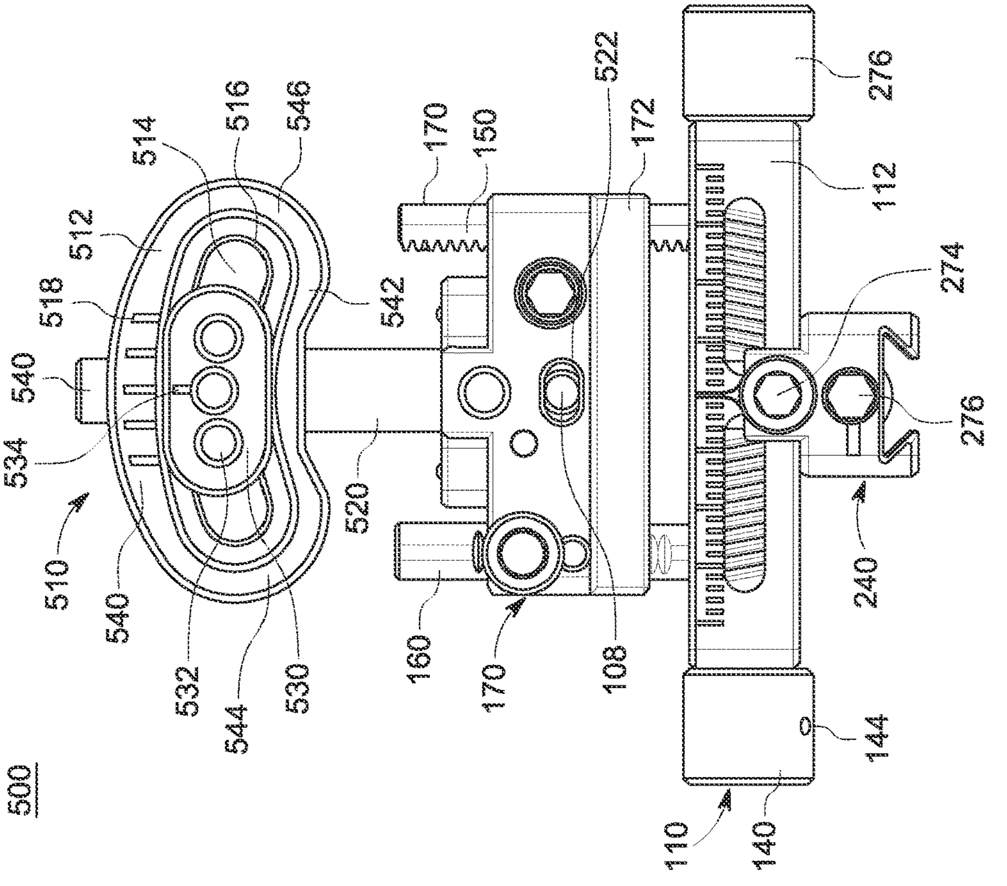
FIG. 26 is a front view of a fast track alignment tibia guide, in accordance with an aspect of the present disclosure.
Figure 29:
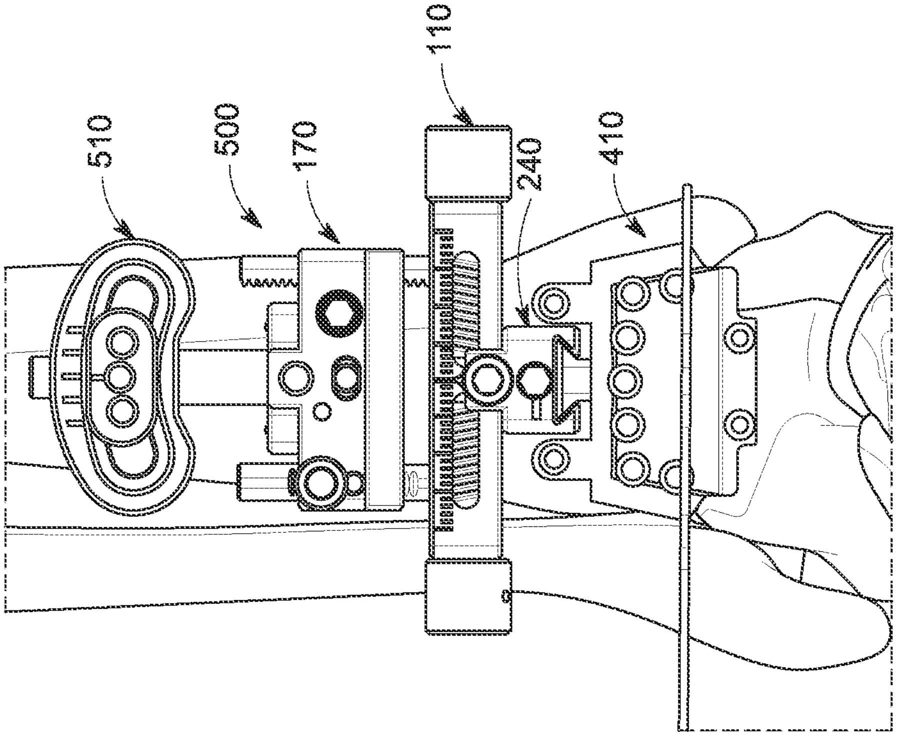
FIG. 29 is a front view of FIG. 28, in accordance with an aspect of the present disclosure.
Figure 28:
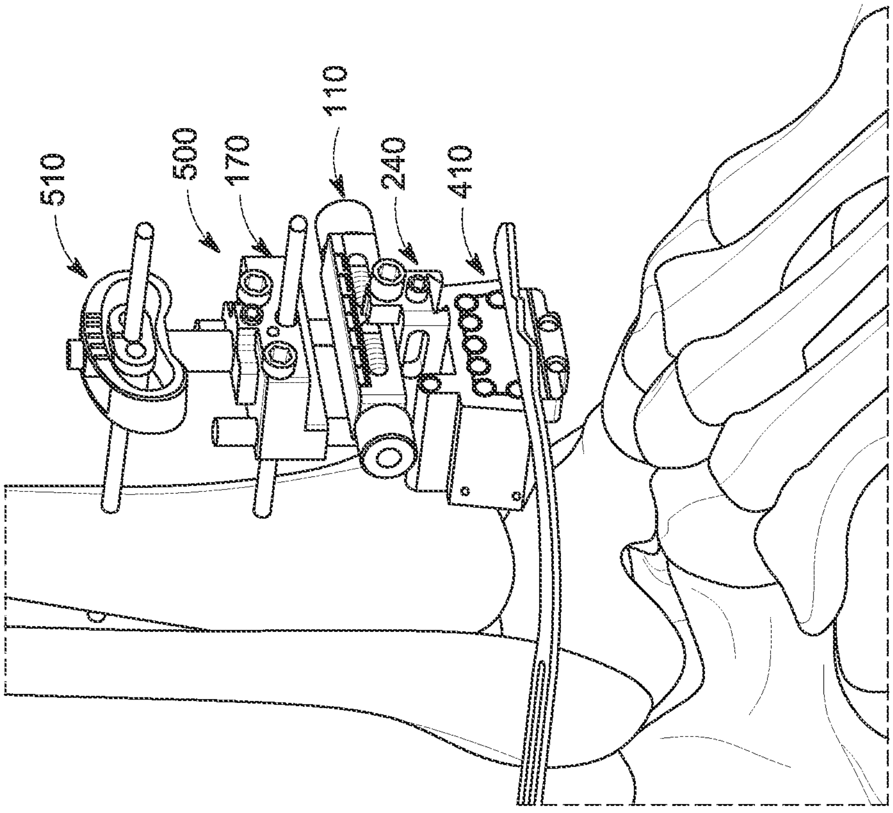
FIG. 28 is a perspective view of the fast track alignment guide of FIG. 1 positioned on a patient's lower extremity with a sizing block coupled to the distal end of the fast track alignment guide and an auxiliary alignment instrument coupled to the sizing block, in accordance with an aspect of the present disclosure.
Figure 30:
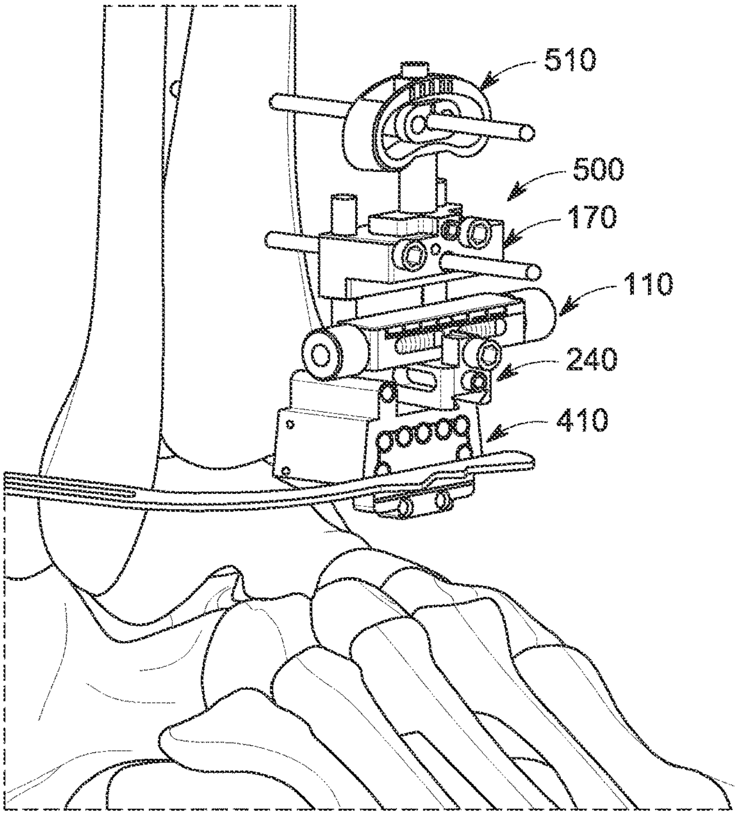
FIG. 30 is another perspective view of the fast track alignment guide of FIG. 28, in accordance with an aspect of the present disclosure.

Referring now to FIGS. 24-25, the alignment guide 100 is shown in use with additional instruments for the TAR procedure. The alignment guide 100 may be used with, for example, other alignment instruments such as a joint line pointer 400. The joint line pointer 400, as well as additional alignment instruments, are described in greater detail in U.S. Provisional Application No. 62/899,655, entitled Alignment Instruments and Methods for Use in Total Ankle Replacement, which is hereby incorporated by reference in its entirety. In addition, as shown in FIG. 25, the alignment guide 100 may be coupled to various resection guides 410. The resection guide 410, as well as additional resection guide and resection instruments, are described in greater detail in U.S. Provisional Application No. 62/898,615, entitled Resection Guides, Sweeping Reamers, and Methods for Use in Total Ankle Replacement, which is hereby incorporated by reference in its entirety.

Although not shown, it is also contemplated that the alignment guide 100 may be used in conjunction with a laser for positioning the alignment guide 100 on the patient's tibia 102 with respect to the ankle joint 106. The laser, as well as alternative lasers, are described in greater detail in PCT Application No. PCT/US2019/029978, entitled Laser-Based Implant Alignment and Resection Guide Systems and Related Methods, which is hereby incorporated by reference in its entirety.

Referring now to FIGS. 26-31, another fast track alignment guide or alignment guide 500 is shown. The alignment guide 500 may include a first translation mechanism 110, a second translation mechanism 170, and a third translation mechanism 510. The first translation mechanism 110 and the second translation mechanism 170 may be, for example, the same or similar to the first and second translation mechanisms 110, 170 as described in greater detail above with respect to the alignment guide 100 and will not be described again here for brevity sake.

With continued reference to FIGS. 26-31, the third translation mechanism 510 may include an adjustment housing 512 which may include a distal member 542 and a proximal member 540 coupled together by a first end member 544 and the second end member 546. The proximal and distal members 540, 542 may each be, for example, curved or arced to form a concave member. The first and second end members 544, 546 may also be, for example, curved or arced to connect the proximal and distal members 540, 542. The adjustment housing 512 may also include a through hole 514 extending from a first side to a second side. The through hole 514 may further include a protrusion or interior track 516 positioned within the through hole 514 and extending away from an interior surface of the adjustment housing 512 to provide a surface for the translating member 520 to translate along. The adjustment housing 512 may also include a plurality of alignment markings 518 positioned between the first end 544 and the second end 546 along at least a portion of the proximal member 540. The translation mechanism 510 may also include a stem 520 extending away from a bottom or distal end of the adjustment housing 512. The stem 520 may include an opening 522. The stem 520 may engage an opening in the second translation mechanism 170 to couple the third translation mechanism 510 to the second translation mechanism 170. Although not shown, a fastener may be inserted into the opening 522 to secure the stem 522 to the opening in the second translation mechanism 170.

The third translation mechanism 510 may also include a translating member 530. The translating member 530 may include at least one through hole 532 for receiving a pin, such as pin 108. As shown, the at least one through hole 532 may be, for example, three through holes 532 positioned relatively linear with each other. The translating member 530 may also include at least one alignment marking 534 which may be used with the alignment markings 518 of the adjustment housing 512 to position the translating member 530 with respect to the adjustment housing 512. In addition, the translating member 530 may include a groove or slot (not shown) for engaging the interior protrusion 516 of the adjustment housing 512. The third translation mechanism 510 may also include a securement member 542 for securing the translating member 530 to the adjustment housing 512 when a desired position is reached.

As shown in FIGS. 28-31, the alignment guide 500 may be coupled to various resection guides 410. The resection guide 410, as well as additional resection guide and resection instruments, are described in greater detail in U.S. Provisional Application No. 62/898,615, entitled Resection Guides, Sweeping Reamers, and Methods for Use in Total Ankle Replacement and U.S. Provisional Application No. 62/898,854 filed Sep. 11, 2019 and entitled Distractors Having Attachable Paddles, Impaction Devices, and Methods for Use in Total Ankle Replacement, which is hereby incorporated by reference in its entirety.

Figure 31:
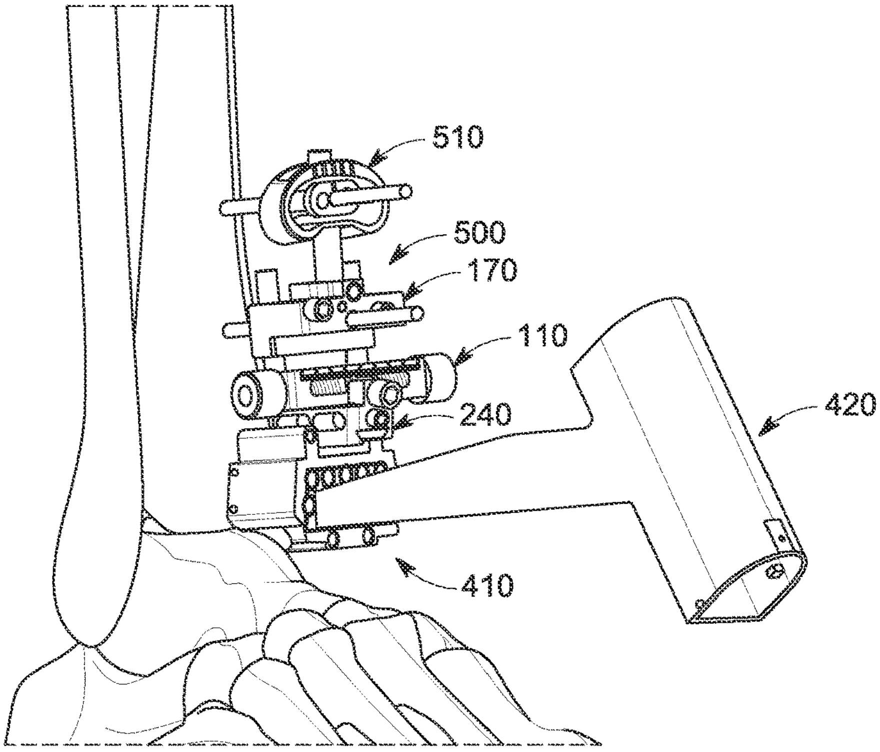
FIG. 31 is a perspective view of a laser alignment guide engaging the fast track alignment guide of FIG. 28, which is coupled to a patient's lower extremity, in accordance with an aspect of the present disclosure.
Figure 33:
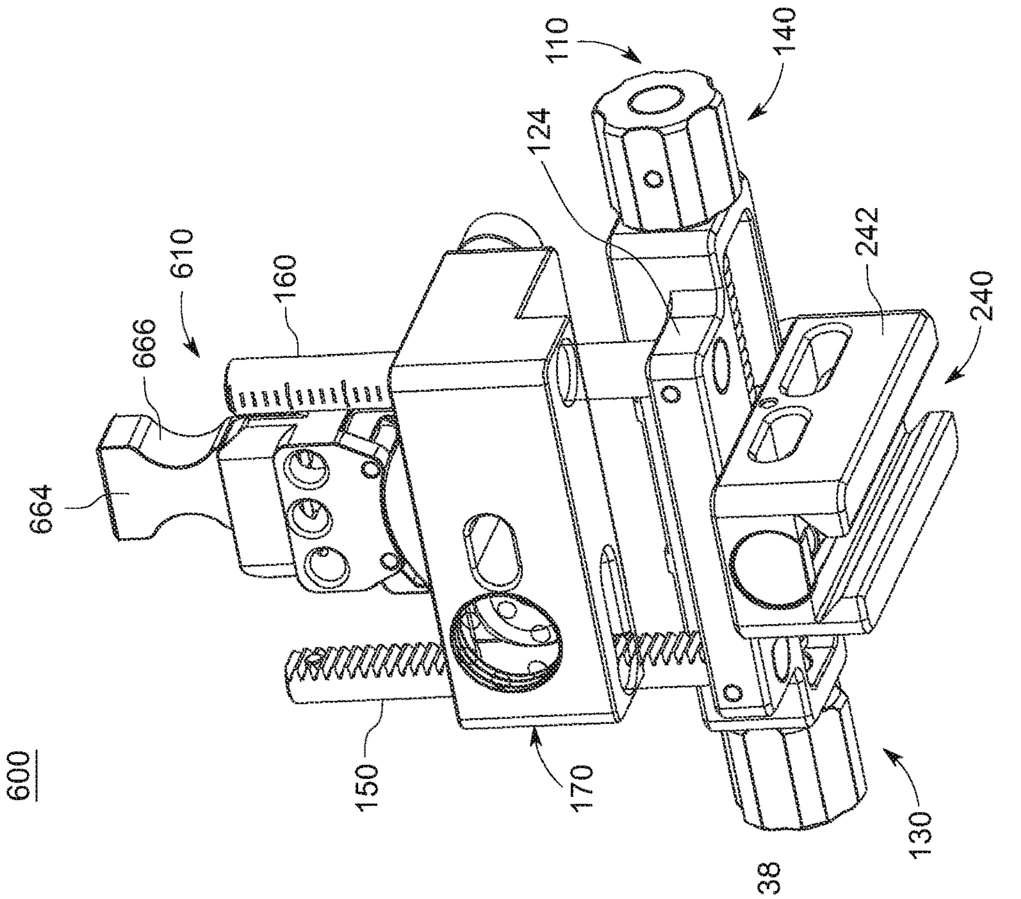
FIG. 33 is a second perspective view of the alignment guide of FIG. 32, in accordance with an aspect of the present disclosure.
Figure 32:
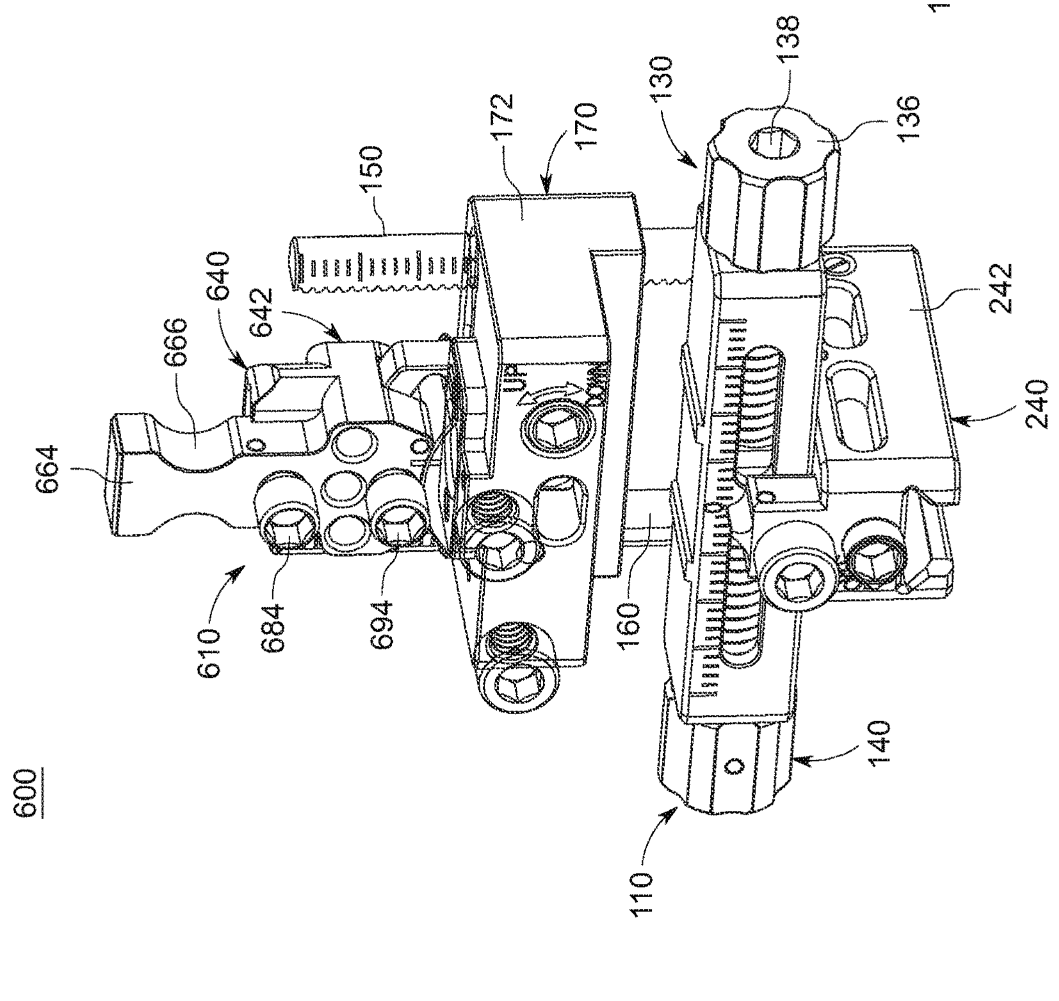
FIG. 32 is a first perspective view of another alignment guide, in accordance with an aspect of the present disclosure.
Figure 35:
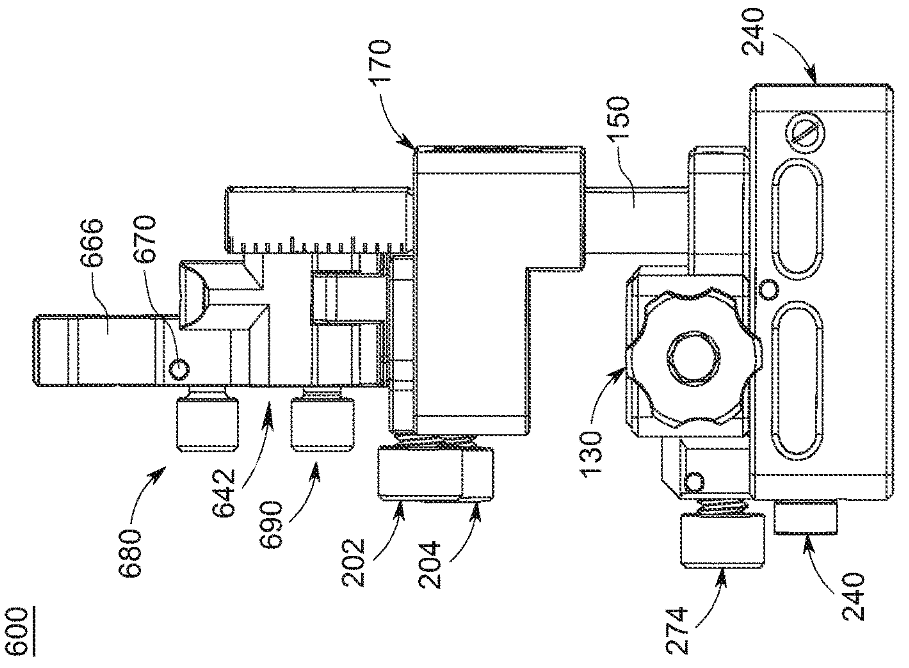
FIG. 35 is a first end view of the alignment guide of FIG. 32, in accordance with an aspect of the present disclosure.
Figure 34:
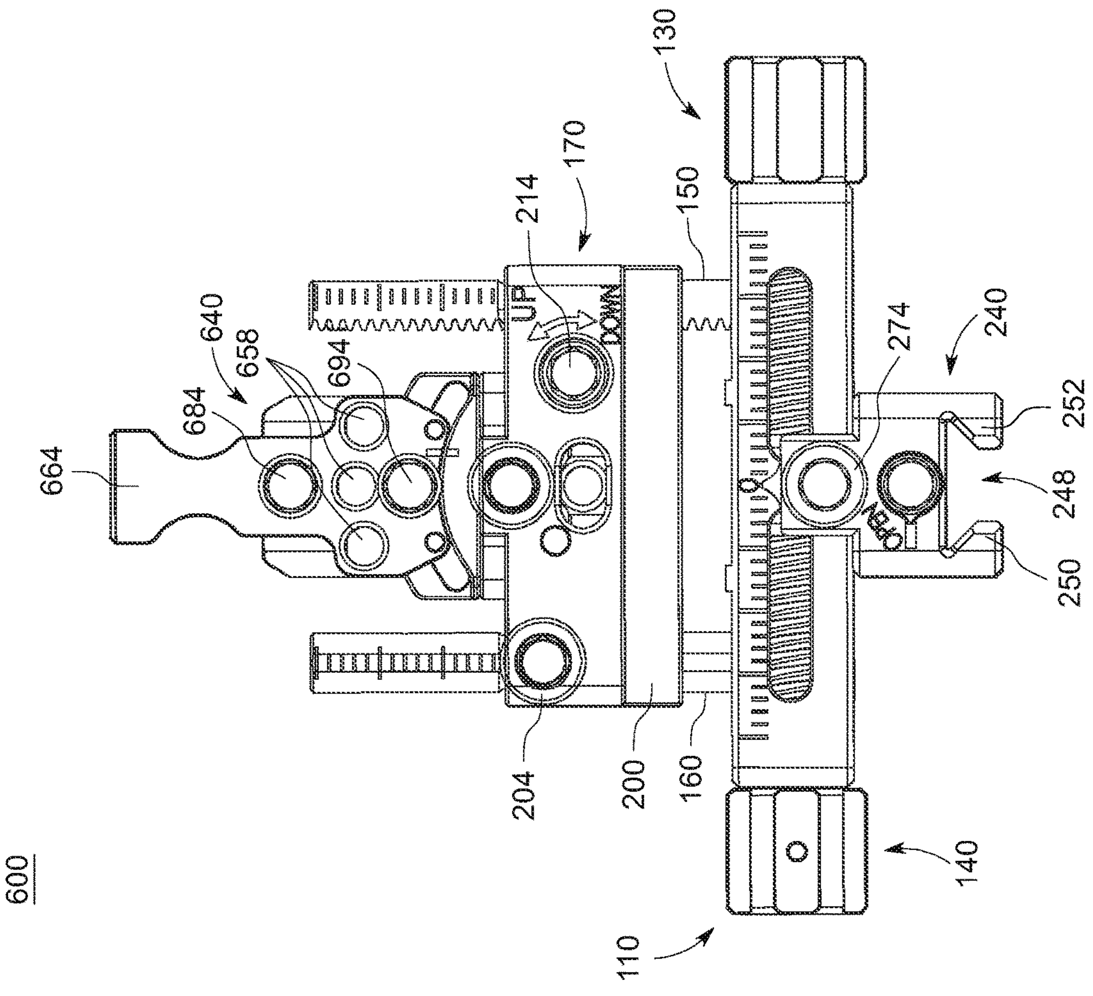
FIG. 34 is a first side view of the alignment guide of FIG. 32, in accordance with an aspect of the present disclosure.
Figure 37:
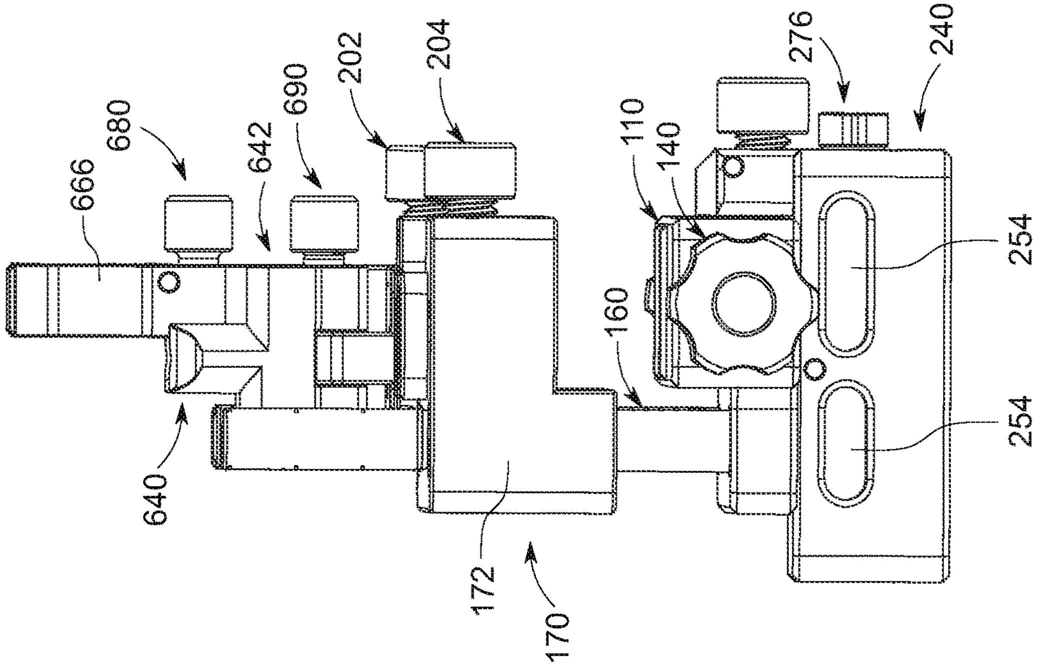
FIG. 37 is a second end view of the alignment guide of FIG. 32, in accordance with an aspect of the present disclosure.
Figure 36:
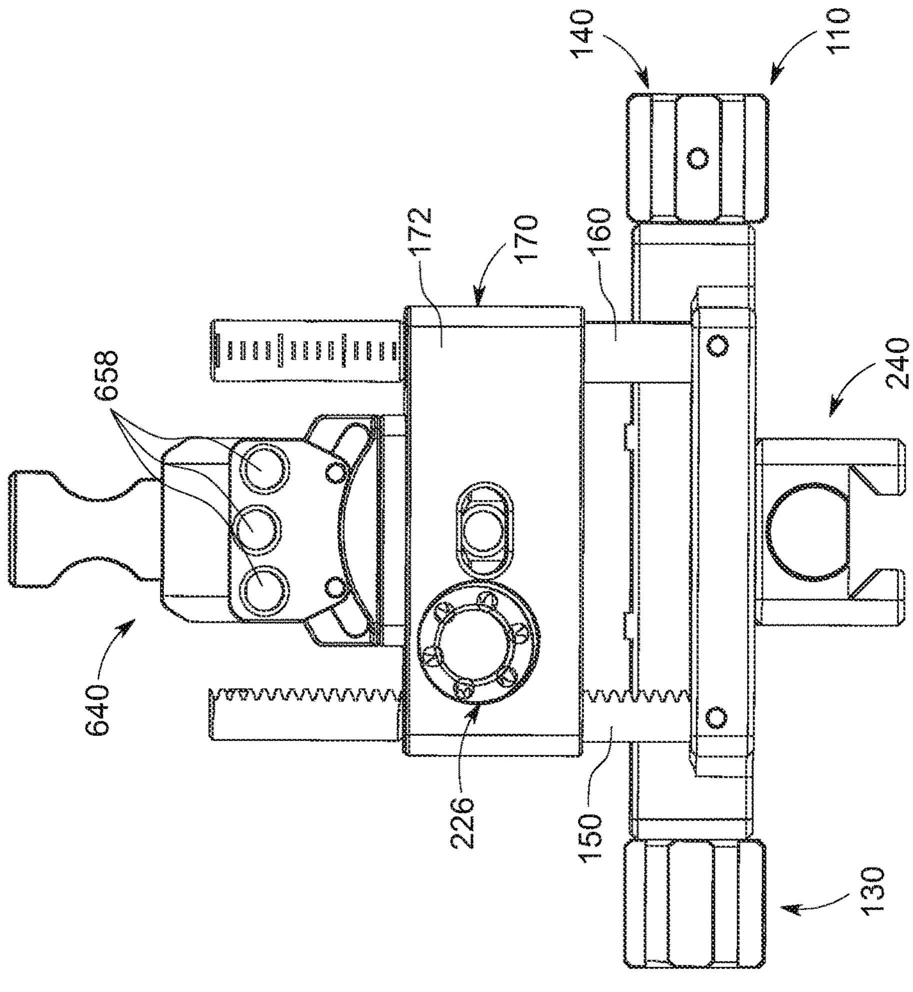
FIG. 36 is a second side view of the alignment guide of FIG. 32, in accordance with an aspect of the present disclosure.
Figure 38:
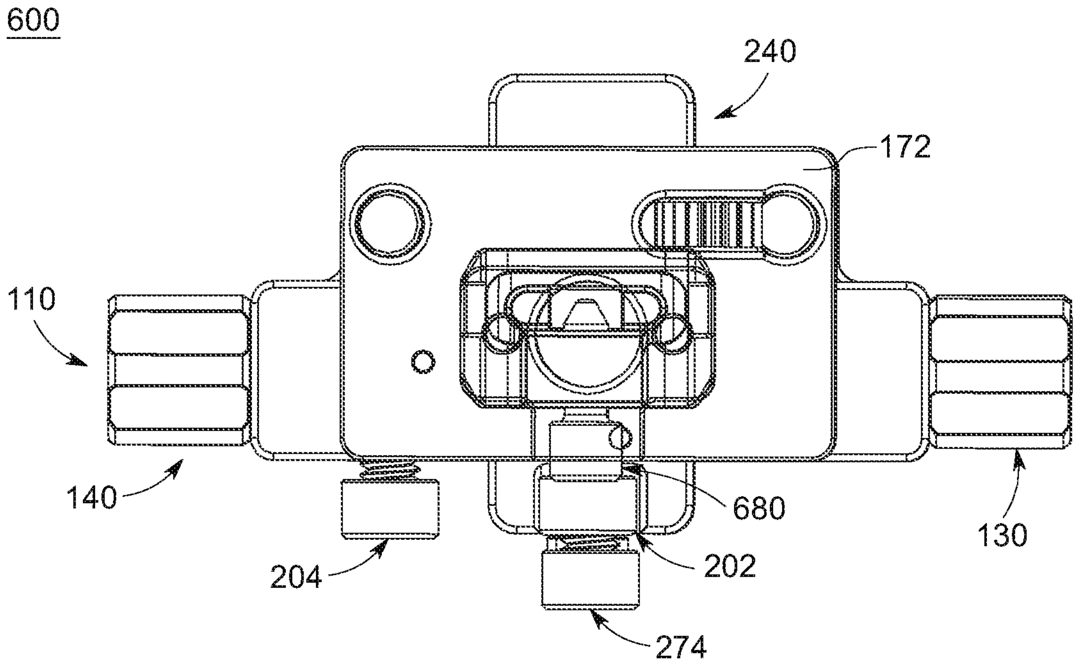
FIG. 38 is a top view of the alignment guide of FIG. 32, in accordance with an aspect of the present disclosure.
Figure 39:
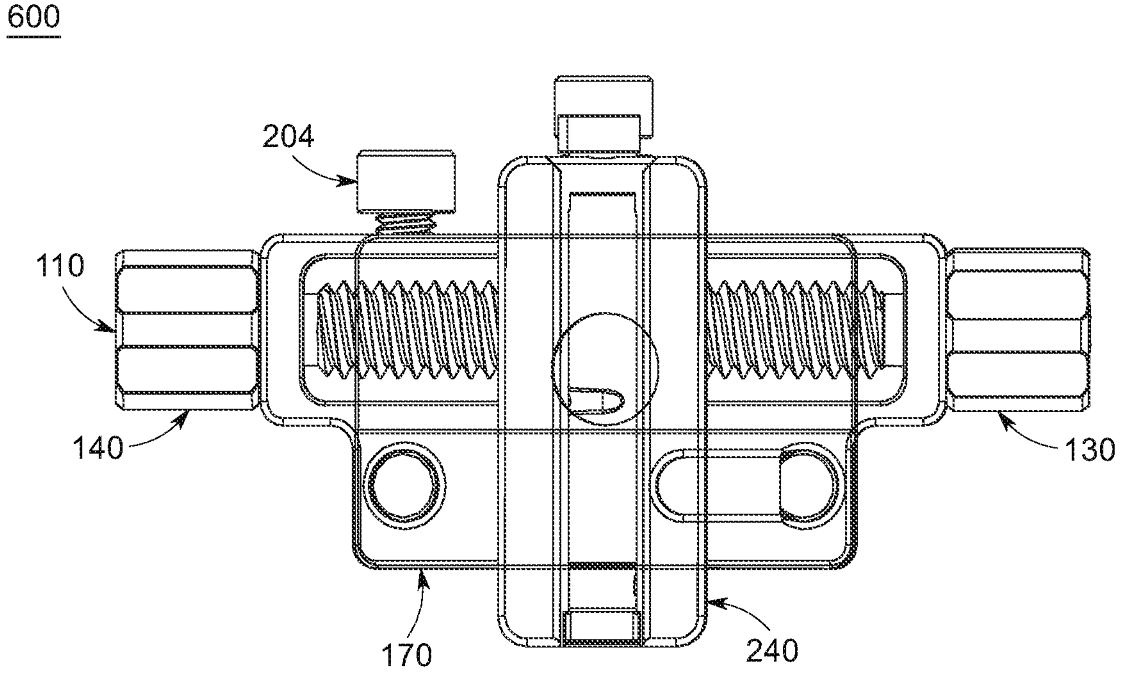
FIG. 39 is a bottom view of the alignment guide of FIG. 32, in accordance with an aspect of the present disclosure.
Figure 41:
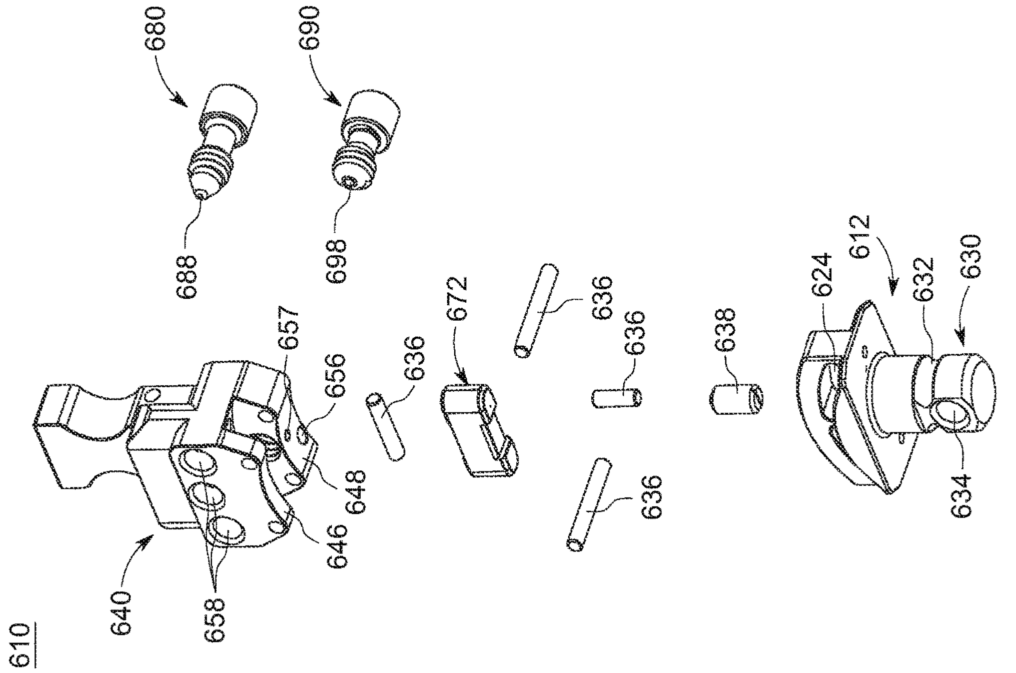
FIG. 41 is an exploded, second perspective view of the third translation mechanism of the alignment guide of FIG. 32, in accordance with an aspect of the present disclosure.
Figure 40:
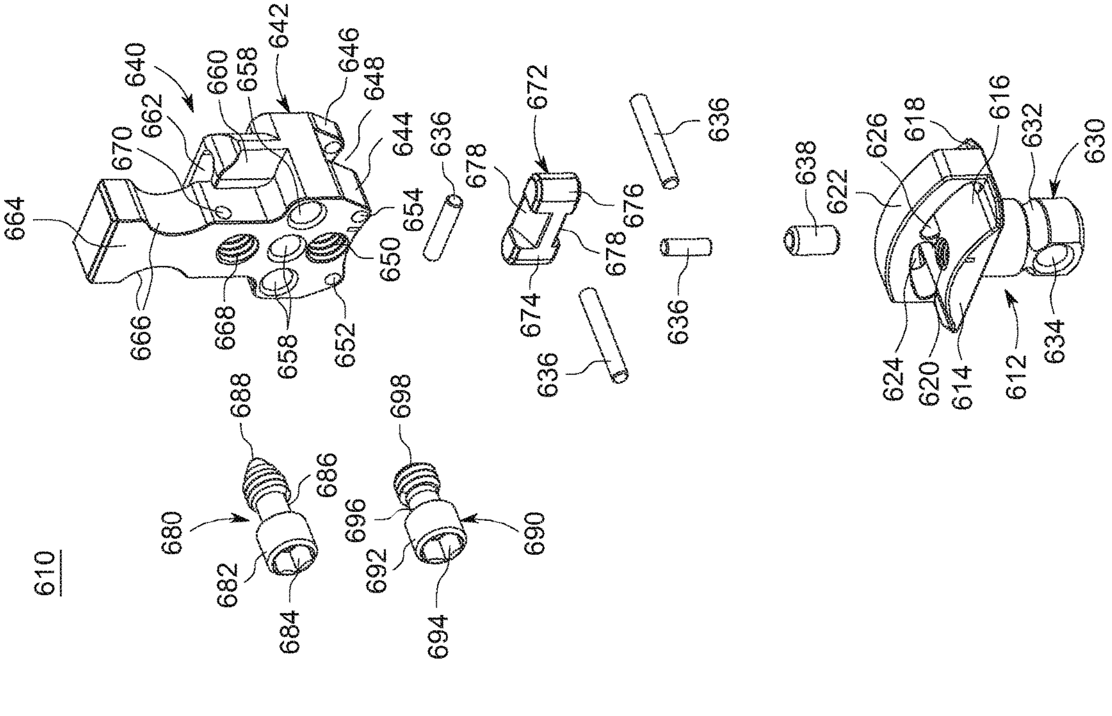
FIG. 40 is an exploded, first perspective view of a third translation mechanism of the alignment guide of FIG. 32, in accordance with an aspect of the present disclosure.
Figure 43:
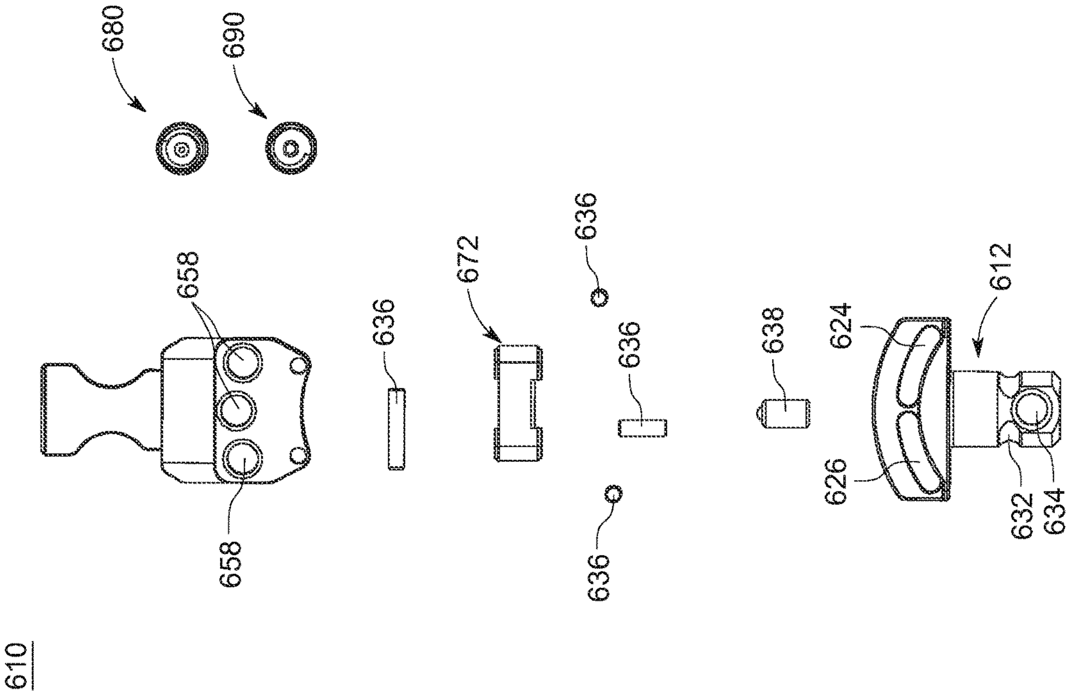
FIG. 43 is an exploded, second side view of the third translation mechanism of the alignment guide of FIG. 32, in accordance with an aspect of the present disclosure.
Figure 42:
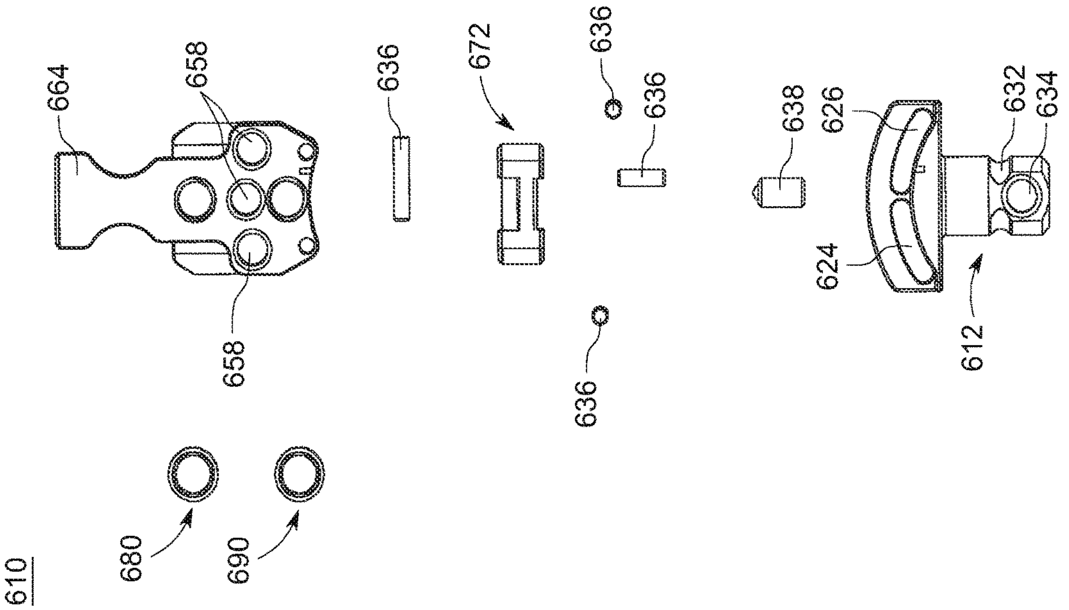
FIG. 42 is an exploded, first side view of the third translation mechanism of the alignment guide of FIG. 32, in accordance with an aspect of the present disclosure.
Figure 45:
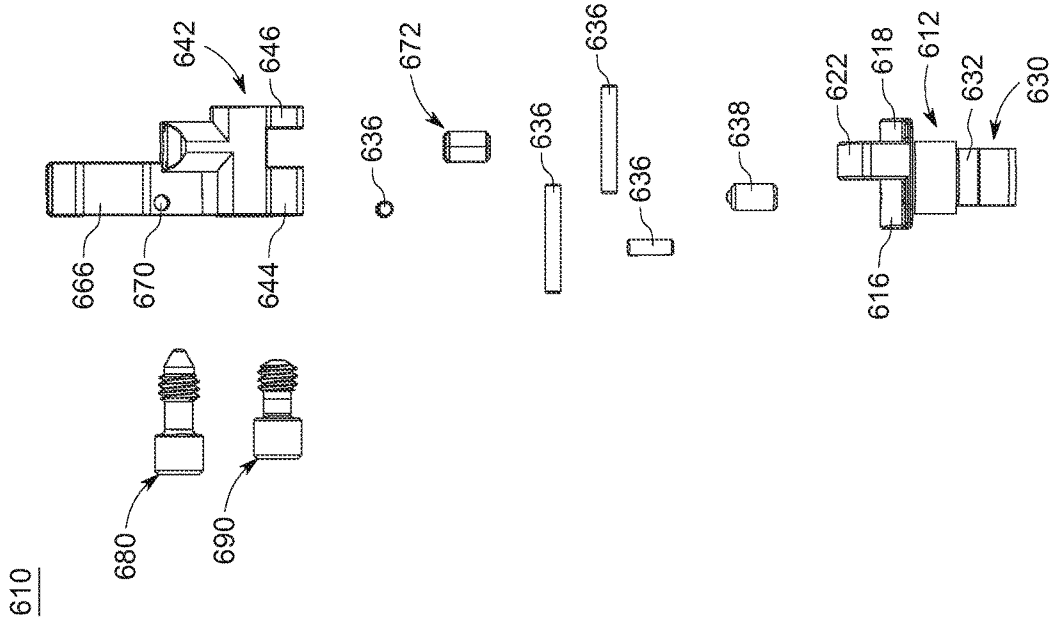
FIG. 45 is an exploded, second end view of the third translation mechanism of the alignment guide of FIG. 32, in accordance with an aspect of the present disclosure.
Figure 44:
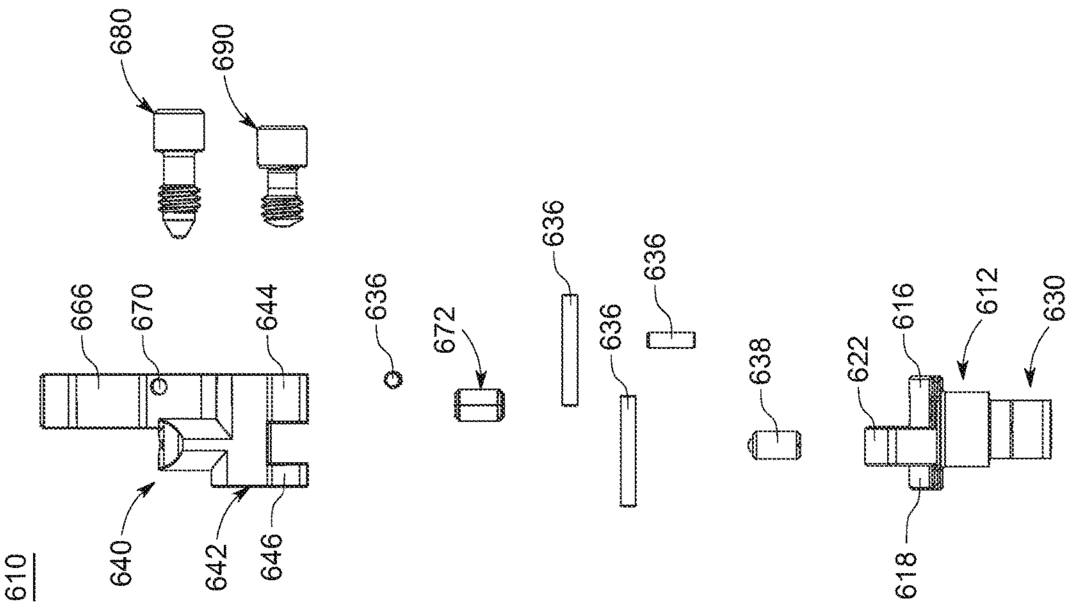
FIG. 44 is an exploded, first end view of the third translation mechanism of the alignment guide of FIG. 32, in accordance with an aspect of the present disclosure.

As shown in FIG. 31, the alignment guide 500 may be used in conjunction with a laser 420 for positioning the alignment guide 500 on the patient's tibia 102 with respect to the ankle joint 106. The laser 420, as well as alternative lasers, are described in greater detail in PCT Application No. PCT/US2019/029978, entitled Laser-Based Implant Alignment and Resection Guide Systems and Related Methods, which is hereby incorporated by reference in its entirety.

Further although not shown, the alignment guide 500 may be used with additional instruments for the TAR procedure. The alignment guide 500 may be used with, for example, other alignment instruments such as a joint line pointer 400, as shown in described with respect to alignment guide 100. The joint line pointer 400, as well as additional alignment instruments, are described in greater detail in U.S. Provisional Application No. 62/899,655, entitled Alignment Instruments and Methods for Use in Total Ankle Replacement, which is hereby incorporated by reference in its entirety.

The alignment guide 500 may slide over the bone pins and be used for alignment and resection of the patient's ankle joint 106. The alignment guide 500 allows for varus-valgus alignment using the third translation mechanism 510. In addition, the alignment guide 500 allows for adjustment of internal-external rotation, as described in greater detail above with reference to alignment guide 100. Finally, the alignment guide 500 allows for distal-proximal and medial-lateral adjustment, as described in greater detail above with reference to alignment guide 100.

Referring now to FIGS. 32-48, another fast track alignment guide or alignment guide 600 is shown. The alignment guide 600 may include a first translation mechanism 110, a second translation mechanism 170, and a third translation mechanism 610. The second translation mechanism 170 is movably coupled to the first translation mechanism 110 by distal proximal translating members 150, 160. The third translation mechanism 600 is detachably coupled to the second translation mechanism 170. The first translation mechanism 110 and the second translation mechanism 170 may be, for example, the same or similar to the first and second translation mechanisms 110, 170 as described in greater detail above with respect to the alignment guide 100 and will not be described again here for brevity sake.

Referring now to FIGS. 40-45, the third translation mechanism or varus-valgus adjustment member 610 is shown. The third translation mechanism 610 may include an adjustment housing 612, a translating member 640 which translatably couples and/or slidably couples to the adjustment housing 612, a first fastener or locking knob 680 rotatably coupled to the translating member 640, and a second fastener or locking member 690 for securing the adjustment housing 612 and the translating member 640 in a desired position.

The adjustment housing 612 may include a base portion 614 with a top surface and a bottom surface opposite the top surface. The top surface of the base portion 614 including a first translating surface 616 and a second translating surface 618 separated by an arm member 622. The first and second translating surfaces 616, 618 may be, for example, curved or arced between a first end and a second end of the adjustment housing 612. The bottom surface of the base portion 614 may be, for example, flat or planar. The base portion 614 may also include a hole, threaded hole, or locking hole 620 extending from the top surface into the base portion 614 on the side of the first translating surface 616. The hole 620 may receive, for example, an alignment member or ball detent 638 for engaging the translating member 640 in a neutral position. The arm member 622 may extend away from the top surface of the base portion 614 in a superior direction. The arm member 622 may include a top surface positioned above or superior to the first and second translating surfaces 616, 618 and the top surface of the arm member 622 may be, for example, curved or arced to match the curve or arc of the first and second translating surfaces 616, 618. The arm member 622 may also include, for example, at least one slot 624, 626 extending through a lower portion of the arm member 622. The at least one slot 624, 626 may extend through the arm member 622 from a first or anterior side to a second or posterior side. The at least one slot 624, 626 may be, for example, a first slot 624 positioned on a first end of the adjustment housing 612 and a second slot 626 positioned on a second end of the adjustment housing 612. The first and second slots 624, 626 may be, for example, separated by a portion of the arm member 622. Each slot 624, 626 may be, for example, sized and shaped to receive a pin or locking pin 636 and the pins 636 may translate along each slot 624, 626.

The adjustment housing 612 may also include a stem or coupling stem 630 extending away from a bottom surface of the base portion 614. The stem 630 may include a groove 632 extending around at least a portion of the circumference of the stem 630. The groove 632 may be, for example, configured or sized and shaped to engage a pin or locking pin, such as pins 636. The stem 630 may also include a through hole 634 extending through the stem 630 from the first side to a second side. The through hole 634 may be, for example, configured or sized and shaped to receive a coupling fastener 202 of the second translation mechanism 170 to couple the third translation mechanism 610 to the second translation mechanism 170.

The translating member 640 may include a body 642 with a first inferior protrusion 644, a second inferior protrusion 646, and a channel 648 separating the first and second inferior protrusions 644, 646. The bottom or inferior surfaces of the first and second inferior protrusions 644, 646 may be, for example, curved or arced between a first end and a second end. The bottom surfaces of the inferior protrusions 644, 646 may be, for example, shaped to correspond to the shape of the top surfaces of the translating surfaces 616, 618 of the adjustment housing 612. The channel 648 may be, for example, sized and shaped or configured to receive the arm member 622 of the adjustment housing 612. When the arm member 622 is inserted into the channel 648, the first protrusion 644 may be positioned adjacent to and/or in sliding engagement with the first translating surface 616 and the second protrusion 646 may be positioned adjacent to and/or in sliding engagement with the second translating surface 618. The translating member 640 may also include a first opening or first locking pin opening 652 and a second opening or second locking pin opening 654 extending through both the first and second inferior protrusions 644, 646. The openings 652, 654 may be, for example, sized and shaped or configured to receive the pins 636 to secure the translating member 640 to the adjustment housing 312. The openings 652, 654 may also align with the slots 624, 626, respectively, to allow the pins 636 to extend through the first protrusion 644, one of the slots 624, 626, and the second protrusion 646. The translating member 640 may also include a first threaded opening or locking hole 650 extending through the first protrusion 644 from a first or anterior surface to a second or posterior surface of the first protrusion 644. The first protrusion 644 may also include a third opening or third locking pin opening 656 extending into the first protrusion 644 from the bottom or inferior surface of the translating member 640. The third opening 656 may be, for example, sized and shaped or configured to receive a pin 636. A portion of the third opening 656 may, for example, overlap with or open into the first threaded opening 650 to engage and assist with retaining the fastener 690 within the opening 650. The bottom or inferior surface of the first protrusion 644 may also include an alignment opening 657. The alignment opening 657 may extend from the bottom surface of the first protrusion 644 into the opening 650. The alignment opening 657 may be, for example, sized and shaped or configured to engage a portion of the alignment member 638 extending out of the hole 620 of the adjustment housing 612. The body 642 may also include at least one through hole or alignment pin hole 658 extending through the body 642 from the first or anterior side to the second or posterior side of the body 642. The at least one hole 658 may be, for example, three holes 658. The holes 658 may be, for example, positioned linearly or almost linearly between the first end and the second end of the body. The holes 658 may be, for example, positioned in a slightly arced or curved orientation to match or correspond to the curve of the bottom surfaces of the protrusions 646, 648.

The translating member 640 may also include a first superior protrusion or first protrusion 660 and a tower 664 both extending away from a top surface of the body 642. The first protrusion 660 may include a passageway 662 extending through the first protrusion 660 from a top or superior surface of the first protrusion 660, through the first protrusion 660, and overlapping or engaging at least a portion of at least one of the through holes 658. In the depicted embodiment, the passageway 662 extends into at least the medial and lateral through holes 658. The tower 664 may be positioned, for example, next to and anterior to the first protrusion 660. The tower 664 may, for example, extend into or overlap a portion of the first protrusion 660. The tower 664 may include at least two recessed regions 666 inset into the tower 664 near a superior end. The tower 664 may also include a hole, threaded hole or locking hole 668 extending into the tower 664 from a first or anterior surface at a position inferior to or below the recessed regions 666. The hole 668 may extend through the tower 664 and into the passageway 662. The tower 664 may also include a fourth locking pin opening 670 extending from a second end of the tower 664 into the tower 664 in a direction perpendicular to the hole 668. The fourth opening 670 may be, for example, sized and shaped or configured to receive a pin 636. A portion of the fourth opening 670 may, for example, overlap with or open into the hole 668 to engage and assist with retaining the fastener 680 within the opening 668.

Figure 46:
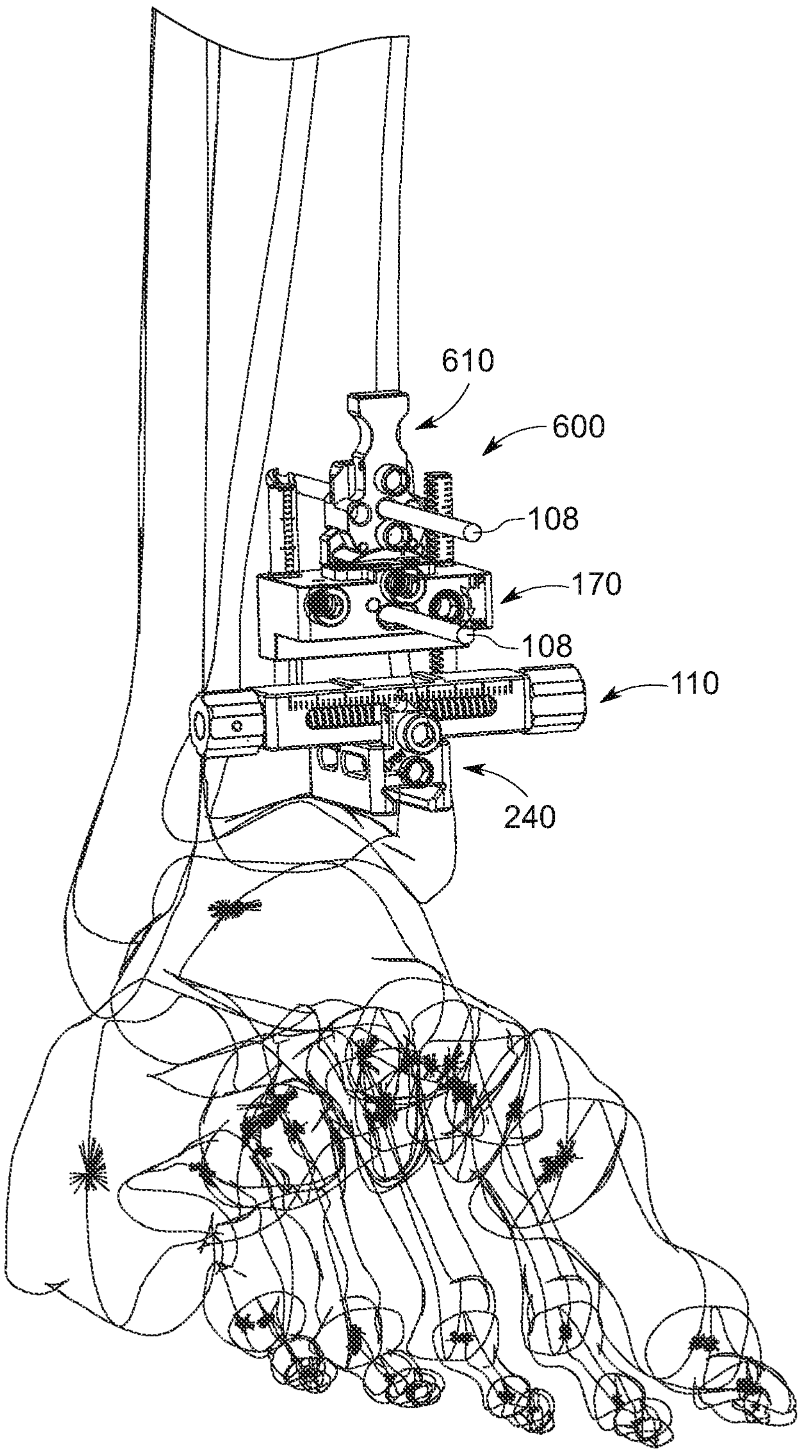
FIG. 46 is a first perspective view of the alignment guide of FIG. 32 positioned on a patient's lower extremity, in accordance with an aspect of the present disclosure.
Figure 47:
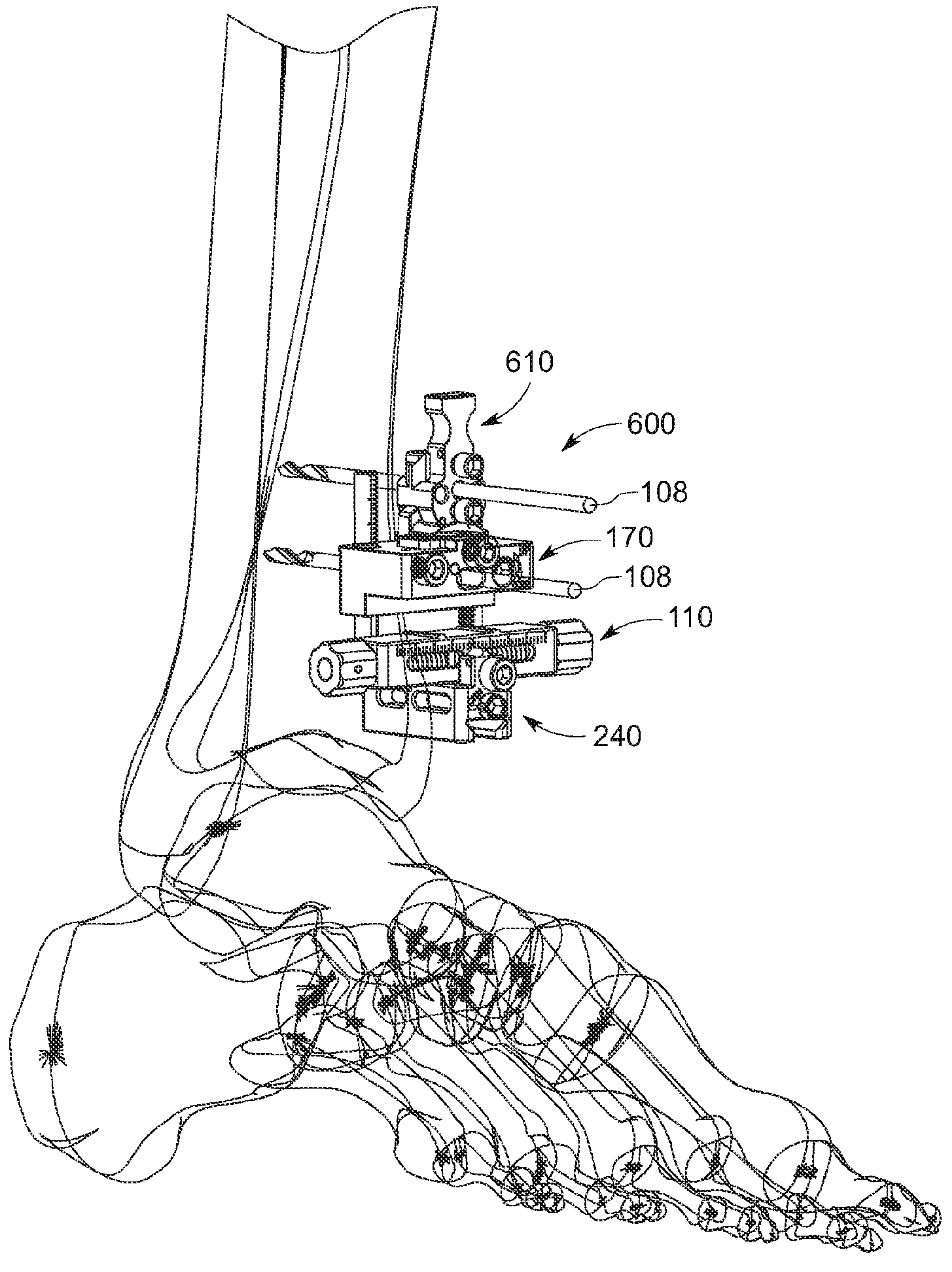
FIG. 47 is a second perspective view of the alignment guide of FIG. 32 positioned on a patient's lower extremity, in accordance with an aspect of the present disclosure.
Figure 48:
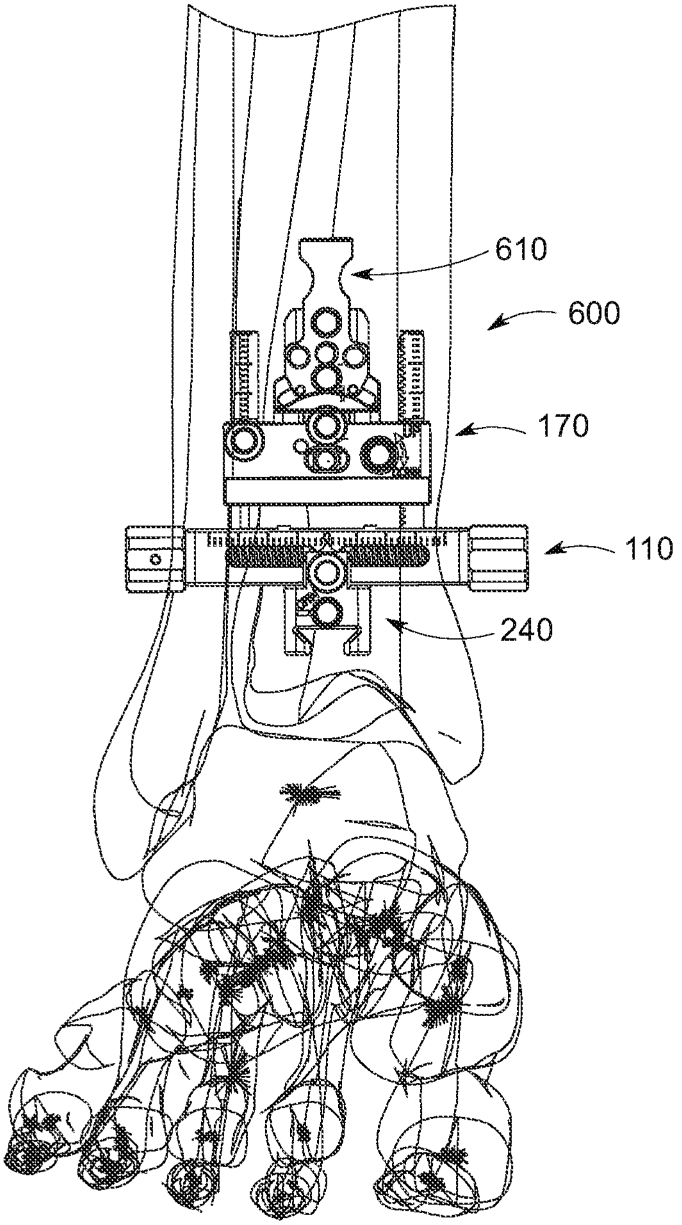
FIG. 48 is a side view of the alignment guide of FIG. 32 positioned on a patient's lower extremity, in accordance with an aspect of the present disclosure.

The third translation mechanism 610 may also include a securement member or securement block 672 configured or sized and shaped to be received within the passageway 662. The securement member 672 may be used, for example, to secure the third translation mechanism 610 to pins 108, as shown in FIGS. 46-48. The securement member 672 may include a first end 674 and a second end 676. The securement member 672 may also include a tapered regions or tapered surfaces 678 positioned between the first end 674 and the second end 676. The tapered regions 678 may form, for example, a wedge-shaped. As shown, the tapered region 678 may include a first taper on the top surface and a second taper on the bottom surface. The tapered surface 678 may be, for example, configured or sized and shaped to engage the fastener 680.

The first fastener or varus-valgus locking knob 680 may include a head 682 at a first end and a shaft 686 extending away from the second end of the head 682 to the second end. The fastener 680 may also include a drive feature 684 recessed in the first end of the head 682. In addition, the fastener 680 may be threaded along at least a portion of the length of the shaft 686. The shaft 686 may also include an engagement tip 688 at the second end. The engagement tip 688 may be, for example, pointed or tapered to engage the tapered surface 678 of the securement member 672.

The second fastener 690 may include a head 692 at a first end and a shaft 696 extending away from the second end of the head 692 to the second end. The fastener 690 may also include a drive feature 694 recessed in the first end of the head 692. In addition, the fastener 690 may be threaded along at least a portion of the length of the shaft 696. The shaft 696 may also include an engagement tip 698 at the second end. The engagement tip 698 may be, for example, blunt or slightly tapered to engage the second arm 622 of the adjustment housing 612.

The alignment guide 600 may be assembled by securing the third translation mechanism 610 to the housing 172 of the second translation mechanism 170 by inserting the alignment pins 206, 208 into the threaded recesses 198 and inserting coupling stem 630 of the adjustment housing 612 into the coupling hole 196 of the housing 172. The coupling fastener 202 may be inserted through fastener hole 192 and the housing 172 to engage the through hole 634 in the stem 630 of the adjustment housing 612. A locking pin may further be inserted through the hole 194 and the housing 172 to retain the coupling fastener 202 within the fastener hole 192 in both unengaged and unengaged position. The translating member 640 may then be coupled to the adjustment housing 612 by aligning the channel 648 of the translating member 640 with the arm member 622 of the adjustment housing 612. The first and second protrusions 644, 646 may be positioned adjacent to the first and second translating surfaces 616, 618, respectively. Locking pins 636 may be inserted through the holes 652, 654 of the translating member 640 as well as through the slots 624, 626 of the adjustment housing 612 to couple the translating member 640 to the adjustment housing 612. When in an unlocked position the pins 636 of the translating member 640 may slide along the slots 624, 626 of the adjustment housing 612. Once the desired varus-valgus position is achieved the translating member 640 may be locked to the adjustment housing 612 by the fastener 690. In addition, before or after determining the desired varus-valgus position the fastener 680 and the locking member 672 may be used to secure the third translation mechanism 610 and any coupled instruments to a pin 108 inserted into a patient's bone.

Referring now to FIGS. 46-48, the alignment guide 600 is positioned on a patient's tibia 102 with two pins 108 and aligned with the ankle joint 106 to allow for a TAR procedure to be performed on the tibia 102 and the talus 104. Once positioned on the tibia 102, the first translation mechanism 110 may be used to achieve medial-lateral adjustment, the second translation mechanism 170 may be used to achieve distal-proximal adjustment, and the third translation mechanism 610 may be used to achieve varus-valgus adjustment. The surgical method may be as described in greater detail in U.S. Provisional Application No. 62/899,460, entitled Total Ankle Replacement Surgical Method, which is hereby incorporated by reference in its entirety.

Although not shown, the alignment guide 600 may also be used with additional instruments for the TAR procedure. The alignment guide 600 may be used with, for example, other alignment instruments such as a joint line pointer 400, shown in FIGS. 24-25. The joint line pointer 400, as well as additional alignment instruments, are described in greater detail in U.S. Provisional Application No. 62/899,655, entitled Alignment Instruments and Methods for Use in Total Ankle Replacement, which is hereby incorporated by reference in its entirety. In addition, the alignment guide 600 may be coupled to various resection guides 410, such as those shown in FIG. 25. The resection guide 410, as well as additional resection guide and resection instruments, are described in greater detail in U.S. Provisional Application No. 62/898,615, entitled Resection Guides, Sweeping Reamers, and Methods for Use in Total Ankle Replacement, which is hereby incorporated by reference in its entirety. It is also contemplated that the alignment guide 600 may be used in conjunction with a laser for positioning the alignment guide 600 on the patient's tibia 102 with respect to the ankle joint 106. The laser, as well as alternative lasers, are described in greater detail in PCT Application No. PCT/US2019/029978, entitled Laser-Based Implant Alignment and Resection Guide Systems and Related Methods, which is hereby incorporated by reference in its entirety.

Additionally the alignment guides 100, 500, 600 may be used with or as described in International Application No. PCT/US2019/029009 filed Apr. 24, 2019 and entitled Implants and Methods of Use and Assembly, U.S. Provisional Application No. 62/779,092 filed Dec. 13, 2018 and entitled Instruments, Guides and Related Methods for Total Ankle Replacement, International Application No. PCT/US2019/066404 filed Dec. 13, 2019 and entitled Instruments, Guides and Related Methods for Total Ankle Replacement, U.S. Provisional Application No. 62/890,611 filed Aug. 22, 2019 and entitled Patient Specific Instruments and Methods of Use, International Application No. PCT/US2019/066336 filed Dec. 13, 2019 and entitled Patient Specific Instruments and Methods of Use, International Application No. PCT/US2019/066149 filed Dec. 13, 2019 and entitled Alignment Instruments and Methods for Use in Total Ankle Replacement, U.S. Provisional Application No. 62/899,740 filed Sep. 12, 2019 and entitled Joint Replacement Alignment Guides, Systems and Methods of Use and Assembly, International Application No. PCT/US2019/066393 filed Dec. 13, 2019 and entitled Joint Replacement Alignment Guides, Systems and Methods of Use and Assembly, International Application No. PCT/US2019/

064948 filed Dec. 6, 2019 and entitled Resection Guides, Sweeping Reamers, and Methods for Use in Total Ankle Replacement, U.S. Provisional Application No. 62/898,854 filed Sep. 11, 2019 and entitled Distractors Having Attachable Paddles, Impaction Devices, and Methods for Use in Total Ankle Replacement, International Application No. PCT/US2019/066398 filed Dec. 13, 2019 and entitled Distractors Having Attachable Paddles, Impaction Devices, and Methods for Use in Total Ankle Replacement, U.S. Provisional Application No. 62/899,646 filed Sep. 12, 2019 and entitled Trial Insert Assembly, International Application No. PCT/US2019/065025 filed Dec. 6, 2019 and entitled Trial Insert Assembly, International Application No. PCT/US2019/066409 filed Dec. 13, 2019 and entitled Total Ankle Replacement Surgical Method, which are each hereby incorporated herein in their entireties.

As may be recognized by those of ordinary skill in the art based on the teachings herein, numerous changes and modifications may be made to the above-described and other embodiments of the present disclosure without departing from the scope of the disclosure. The components of the implants as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the implants may include more or fewer components or features than the embodiments as described and illustrated herein. For example, the components and features of FIGS. 1-25, FIGS. 26-31, FIGS. 32-48, and FIGS. 49-62 may be used interchangeably and in alternative combinations as would be modified or altered by one of skill in the art. Specifically, alignment guides 100, 500, 600 may be used in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A method of using an alignment guide system, comprising:

obtaining the alignment guide system, wherein the alignment guide system comprises:

a first translation mechanism configured to translate in a medial-lateral direction;

a second translation mechanism coupled to the first translation mechanism, wherein the second translation mechanism translates in a distal-proximal direction; and a third translation mechanism coupled to the second translation mechanism, wherein the third translation mechanism translates in a varus-valgus direction;

coupling the alignment guide system to a tibia of a patient, wherein the alignment guide system is coupled to a distal end of the tibia between a midpoint of the tibia and an ankle joint of the patient, and wherein the entire alignment guide system is located between the midpoint of the tibia and the ankle joint of the patient; and translating the alignment guide system in at least one of the medial-lateral direction, the distal-proximal direction, and the varus-valgus direction to position the alignment guide system over the ankle joint.

2. The method of claim 1, further comprising:

releasably coupling a pair of pins with the alignment guide system and the tibia of the patient so as to releasably couple the alignment guide system with the tibia of the patient, wherein each pin of the pair of pins is inserted into the distal end of the tibia between the midpoint of the tibia and the ankle joint.

3. The method of claim 1, further comprising:

manipulating the first translation mechanism to translate the alignment guide system in the medial-lateral direction relative to the tibia of the patient.

4. The method of claim 3, further comprising:

manipulating the second translation mechanism to translate the alignment guide system in the distal-proximal direction relative to the tibia of the patient.

5. The method of claim 4, further comprising:

manipulating the third translation mechanism to translate the alignment guide system in the varus-valgus direction relative to the tibia of the patient.

6. The method of claim 5, further comprising:

securing the third translation mechanism to a pin inserted in the tibia of the patient.

7. The method of claim 6, further comprising:

releasably coupling a laser with at least a portion of the alignment guide system.

8. The method of claim 7, further comprising:

releasably coupling an alignment block with a coupling member, wherein the coupling member is positioned adjacent to the first translation mechanism.

9. The method of claim 1, wherein the translating of the alignment guide system comprises:

translating the alignment guide system in the medial-lateral direction, the distal-proximal direction, and the varus-valgus direction to position the alignment guide system over the ankle joint.

10. A method of using an alignment guide system, comprising:

obtaining the alignment guide system, wherein the alignment guide system comprises:

a first translation mechanism configured to translate in a medial-lateral direction;

a second translation mechanism coupled to the first translation mechanism, wherein the second translation mechanism translates in a distal-proximal direction; and a third translation mechanism coupled to the second translation mechanism, wherein the third translation mechanism translates in a varus-valgus direction;

coupling the alignment guide system to a tibia of a patient, wherein the alignment guide system is coupled to a distal end of the tibia between a midpoint of the tibia and an ankle joint of the patient, and wherein the entire alignment guide system is located between the midpoint of the tibia and the ankle joint of the patient;

determining a desired position in the medial-lateral direction;

translating the alignment guide system to achieve the desired position in the medial-lateral direction;

determining a desired position in the distal-proximal direction;

translating the alignment guide system to achieve the desired position in the distal-proximal direction;

coupling a laser with at least a portion of the alignment guide system;

determining a desired position in the varus-valgus direction; and translating the alignment guide system to achieve the desired position in the varus-valgus direction.

* * * * *